(12) United States Patent
Reichelt et al.

(10) Patent No.: US 8,906,958 B2
(45) Date of Patent: Dec. 9, 2014

(54) COMPOUNDS AND MIXTURES FOR INFLUENCING INFLAMMATORY STATES

(71) Applicant: Symrise AG, Holzminden (DE)

(72) Inventors: Katharina Reichelt, Holzminden (DE); Jakob Ley, Holzminden (DE); Marcus Götz, Oberweser (DE); Maria Blings, Holzminden (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 13/779,046

(22) Filed: Feb. 27, 2013

(65) Prior Publication Data

US 2013/0236472 A1 Sep. 12, 2013

(30) Foreign Application Priority Data

Mar. 2, 2012 (EP) .................................... 12157903

(51) Int. Cl.
*A61K 31/352* (2006.01)
*A61K 31/192* (2006.01)
*A61K 45/06* (2006.01)
*C07D 311/58* (2006.01)
*C07C 65/40* (2006.01)
*A61K 31/353* (2006.01)
*A23L 1/30* (2006.01)
*C07D 311/32* (2006.01)

(52) U.S. Cl.
CPC .............. *A61K 31/192* (2013.01); *A61K 45/06* (2013.01); *A61K 31/353* (2013.01); *A61K 31/352* (2013.01); *C07C 65/40* (2013.01); *A23L 1/3002* (2013.01); *C07D 311/58* (2013.01); *C07D 311/32* (2013.01)
USPC ........... 514/456; 514/568; 549/399; 562/463; 562/473; 562/495

(58) Field of Classification Search
USPC .............. 424/158.1, 93.4; 562/463, 473, 495; 514/568, 456, 171, 150, 263.2, 249; 549/399
See application file for complete search history.

(56) References Cited

U.S. PATENT DOCUMENTS

2013/0251730 A1* 9/2013 Ley et al. .................... 424/158.1

OTHER PUBLICATIONS

Reichelt et al., Identification of Bisprenylated Benzoic Acid Derivatives from Yerba Santa (*Eriodictyon* ssp.) Using Sensory-Guided Fractionation, 2010, J. Agric. Food Chem., 58, 1850-1859.*
Makabe et al., "Myrsinoic Acid E, an Anti-inflammatory Compound from Myrsine seguinii," Biosci. Biotechnol. Biochem., 67(9), pp. 2038-2041 (2003).

* cited by examiner

*Primary Examiner* — Kristin Vajda
(74) *Attorney, Agent, or Firm* — Dilworth & Barrese, LLP

(57) ABSTRACT

The invention relates to certain compounds, salts of these compounds and mixtures containing or consisting of two or more such compounds, two or more such salts or one or more such compounds and one or more such salts, each for use in a method for the prophylaxis and/or treatment of inflammation, in particular of inflammation of the skin.

18 Claims, 1 Drawing Sheet

COMPOUNDS AND MIXTURES FOR INFLUENCING INFLAMMATORY STATES

BACKGROUND OF THE INVENTION

The present invention primarily relates to new uses for the prophylaxis and/or treatment of inflammation, namely compounds of the formula (X)

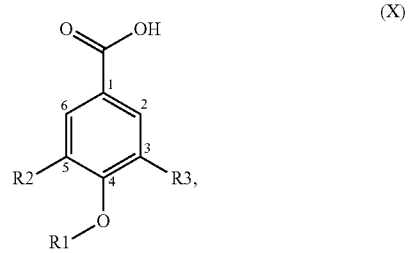

salts of compounds of the formula (X) and mixtures containing or consisting of two or more different compounds of the formula (X), two or more different salts of compounds of the formula (X) or one or more different compounds of the formula (X) and one or more different salts of compounds of the formula (X), wherein for R1, R2 and R3 that herein described, in particular that stated in the claims, applies, for use in a method for the prophylaxis and/or treatment of inflammation, in particular of inflammation of the skin, in particular in a method for reducing the release of TNF-alpha, and/or for reducing the release of an interleukin, preferably of IL-1, IL-6 and/or IL-8, and/or for reducing the release of a prostaglandin, preferably of PGE2, and/or for reducing the release of interferon-gamma and/or NF-κB.

The present invention also relates to preparations, in particular to preparations used for nutrition or enjoyment, pharmaceutical preparations, cosmetic preparations and dermatological preparations, which contain a compound to be used according to the invention, a salt to be used according to the invention or a mixture (as described herein) to be used according to the invention, for use in a method for the prophylaxis and/or treatment of inflammation, in particular of inflammation of the skin, in particular in a method for reducing the release of TNF-alpha, and/or for reducing the release of an interleukin, preferably of IL-1, IL-6 and/or IL-8, and/or for reducing the release of a prostaglandin, preferably of PGE2, and/or for reducing the release of interferon-gamma and/or NF-κB.

Further aspects of the present invention follow from the following description.

There is a constant need to provide inflammation-inhibiting substances for the protection of cells or tissues (of people and animals), in particular of the skin, above all for use in cosmetic preparations, pharmaceutical preparations, foodstuffs or semi-luxury products. In particular there is a constant need to find new substances with anti-inflammatory activity, which support the natural defence mechanisms against inflammation in physiological systems (of people and animals). In this respect, there is particularly great interest in substances from natural extracts. Particularly attractive for use in foods are plants or parts or extracts of plants, which have a long history of edible consumption.

In the context of the present text, the term "skin" comprises not only the (human or animal) skin in the usual sense, but rather cell layers in general which cover internal and/or external surfaces on/in the human or animal body. Accordingly, in the context of the present text, the term "skin" comprises surface and glandular epithelia, i.e. in particular also mucous membranes, e.g. the oral mucosa, the gastric mucosa and the intestinal mucosa. As barrier organs of the (human) body, the mucous membranes are exposed to external influences to a particular extent. They line the various body cavities which are either in contact with the external environment (e.g. mouth and throat) or the internal organs of a body (e.g. intestinal lumen).

Many intrinsic factors (e.g. genetic predisposition) and extrinsic factors (e.g. damage to the skin barrier, influence of UV light, skin-irritant or allergy-triggering substances) can lead to skin irritation or dysfunctions of the skin.

In the context of the present text "skin irritation" is understood to mean any change in the skin, which triggers indisposition ("sensorial malaise"), and/or is characterized by symptoms of dry, reddened and/or inflamed skin. The term "sensorial malaise" also includes states which are associated with pruritus or pains.

Skin irritation can include the following skin conditions: sensitive skin, for example sensitive scalp, easily damaged skin, atopic skin (atopy) and irritated or inflamed skin, which can appear in the form of skin reddening (erythema).

Skin irritation can in particular also concern or comprise
  irritation of the mucous membranes in the oral cavity, for example periodontitis and gingivitis (as described in detail below),
  irritation and infections of the airways (as described in detail below; see also US 2009/0238905 on this), for example rhinosinusitis (common cold), sinusitis and pharyngitis/tonsillitis, and
  irritation of the gastrointestinal tract (as described in detail below; see also US 2009/0238905 on this).

The problem of sensitive skin affects a growing number of adults and children. It is believed that a proportion of up to 50% of the population have sensitive skin (L. Misery et al., Ann. Dermatol. Venereol. 2005, 132, 425-429). Sensitive skin describes skin which has a decreased threshold for irritant substances, and also hyper-reactive, intolerant and also atopic skin. In the case of people with sensitive or easily damaged skin, the so-called "stinging" (Engl. "to sting"=burn, stab, be painful) can be observed. Typical symptoms which are associated with "stinging" or "sensitive skin" in general are skin reddening, tingling, feelings of tension and burning of the skin and pruritus. They can be triggered by certain ambient influences, e.g. massage, influence of surfactants, weather (heat, cold, dryness or high atmospheric humidity), thermal or UV radiation (e.g. emanating from the sun) or even by psychological stress.

Sensitive scalp is also characterized by skin reddening, tingling, burning and stinging. Triggers are for example soap, shampoos or other hair care products, surfactants, water with a high calcium carbonate content and/or (mechanical) stress. Erythema and hyperseborrhoea (excessive sebaceous secretion) of the scalp and dandruff are often accompanied by the said symptoms.

Atopy (atopic syndrome) is observed (with a rising trend) in ca. 10-20% of the population in industrialized countries. This is a hypersensitivity of the skin to substances from the environment with an increased tendency to development of hypersensitivity reactions of the immediate type (allergies) towards substances from the natural environment. It is believed that atopy has genetic causes. Atopy can appear as atopic dermatitis. In this case, the skin barrier is damaged, and the skin is often inflamed and itches.

Periodontitis (as an example of an inflammatory reaction of the gums or the oral mucosa) is an inflammation of the periodontium (dental periosteum), i.e. the tissue which surrounds and supports the teeth. The periodontium consists of various tissues: gingival epithelium (gingiva; gum), connective tissue of the gingiva, dental periosteum (periodontium, desmodontium), dental cement and surrounding alveolar bone. The dental periosteum lies between the surface of the root and the alveolar bone and is a cell-rich connective tissue which holds the teeth in the osseous tooth socket, the alveolus. 53 to 74% of the periodontal gap consists of collagen and oxytalan fibre bundles. Periodontal fibres which are present in the dental cement and in the alveolar bone hold the tooth in the alveolar bone. The main characteristics of periodontitis comprise inflammation of the gum, loss of stability, formation of pockets in the dental periosteum and degradation of the alveolar bone.

The main cause of periodontitis is plaque. This consists of certain components of the saliva, food residues and bacteria and degradation products thereof. This specific form of infectious disease is in most cases caused by *Porphyromonas gingivalis, Bacteroides forsythus* and *Actinobacillus actinomycetemcomitans*. The continuous release of bacterial toxins, in particular lipopolysaccharide (LPS), leads to a non-specific immune defence reaction. LPS-stimulated macrophages release prostaglandin E2 (PGE2) and pro-inflammatory mediators, such as for example interleukins (e.g. IL-1 beta) and TNF-alpha, in the affected tissue of the patient. The pro-inflammatory mediators trigger the release of further PGE2s and matrix-destroying metalloproteinases (matrix metalloproteinases, MMPs) from the invasive fibroblasts, which destroy the extracellular matrix of the surrounding connective tissue. This in turn allows bacteria which are actually in contact with the exposed gum to penetrate deeper into the underlying connective tissue and there to drive the inflammatory process further, so that eventually the junction between the top layer of the epithelium and the root is lost. As a result a pocket in the gum is formed. The body's reaction to this is an inflammation of the gum and the dental periosteum with damage to the alveolar bone. In the final stage of periodontitis, the person affected is at risk of tooth loss.

However, in addition to bacteria, chemical or mechanical damage can also cause irritation or inflammatory reactions of the gum or the oral mucosa. Pro-inflammatory mediators, in particular interleukins such as IL-1 alpha and PGE2, are released in this process (Reilly, D. M. and M. R. Green (1999)).

Irritation and infections of the airways affect the respiratory tract (of people or animals). The respiratory tract is subdivided into three sections: (i) the upper airways, incl. nose and paranasal sinuses and pharynx, (ii) the lower airways with larynx and trachea and (iii) the lungs with bronchi, bronchioles, pulmonary alveoli, etc.

"Irritation and infections of the upper airways" designate in particular an acute infection, which affects the upper airways, nose, sinus, pharynx and/or larynx. In the United States of America, ca. one billion acute diseases of the upper airways are recorded each year. Irritation and infections of the upper airways include rhinosinusitis (common cold), sinusitis, pharyngitis/tonsillitis, laryngitis and sometimes bronchitis. The symptoms of these infections often include swelling of the nasal mucosae, cough, nasal catarrh, sore throat, fever, sneezing and pressure sensation. The symptoms as a rule start 1 to 3 days after contact with pathogenic germs, mostly viruses. The symptoms typically cease in 7 to 10 days, but can also persist for longer.

A commonly occurring (airway) infection is pharyngitis. Pharyngitis is in most cases a painful inflammation of the pharynx and is thus commonly also described as sore throat. Inflammation of the tonsils, tonsil inflammation or tonsillitis can arise at the same time.

For infections of the upper airways there are essentially three therapeutic approaches: symptomatic, remedial and preventive. Symptomatic therapy aims to alleviate symptoms and pain. Remedial therapies are intended to treat the pharyngitis by preventing its spreading and accelerate the healing process. Preventive therapy is intended to prevent the outbreak of an infection.

Remedial therapies are most effective against bacterial infections, e.g. streptococci. Many preventive therapies are also remedial.

With viral infections, the recovery from a pharyngeal inflammation as a rule occurs spontaneously within a few days. Hence the favourite method is symptomatic therapy.

Various non-antibiotic therapies for throat inflammation have been tested in controlled studies. Analgesic therapies are among the most effective here.

The symptomatic therapies for infections of the upper airways include: formulations whose purpose is to act remedially or symptomatically and which can present in the following forms:

solid galenical forms (such as for example tablets (with and without coating, with and without modified release), sugar-coated tablets (with and without coating, with and without modified release), capsules (soft or hard gelatine capsules with and without modified release), granules (with and without modified release), powders (with and without modified release), suppositories (with and without coating, with and without modified release), lozenges and chewing gums), liquid forms (such as for example solutions, suspensions, emulsions, syrups (colloquially cough syrup), mouthwashes, gargle solutions, throat sprays or nasal sprays, nasal drops, nasal rinse solutions, nasal powders, nasal ointments or ear drops, ear sprays, ear rinse solutions, ear powders and aural tampons), semisolid forms (such as for example hydrophobic ointments including for example: hydrocarbon gels, lipogels, silicone gels, oleogels and water-absorbing ointments including for example absorption bases, hydrophilic ointments, hydrophilic gels (hydrogels) or pastes, Inhalants (such as for example compressed gas dispenser inhalers, powder inhalers, inhalers with atomisers, and inhalation concentrates for inhalation), and active substance-containing plasters or other therapeutic systems.

The gastrointestinal tract (also called digestive tract) is the system of internal organs which take up and digest the food, in order to absorb nutrient substances therefrom, to obtain energy and to excrete the food components remaining. Accordingly, the main functions of the digestive tract are food uptake, digestion, absorption and excretion.

The upper digestive tract consists of the mouth, pharynx, oesophagus and stomach. The mouth contains the oral mucosae, which contain the openings of the saliva glands, the tongue and the teeth. Behind the mouth lies the pharynx, which leads to a hollow muscular tube, the oesophagus, which in turn leads into the stomach. The small intestine is joined to the stomach. The lower digestive tract consists of the intestines and the anus.

The intestines consist of the intestine, the small intestine, which consists of three parts, duodenum, jejunum and ileum, the large intestine, which also consists of three sections, caecum with vermiform appendix (blind gut), the colon (rising colon, transverse colon and descending colon) and the rectum.

The commonest inflammatory conditions of the digestive tracts include gastro-oesophageal reflux diseases, heartburn and gastric ulcers. The therapy usually includes firstly reduction of the symptoms and reduction of the inflammation in the tissue and secondly longer-term therapies in order to prevent reappearance of the symptoms.

Other inflammatory diseases of the digestive system, inter alia, are milder inflammatory diseases such as irritable bowel syndrome (IBS) and inflammatory diseases of unknown aetiology and chronic inflammatory intestinal diseases (IBD), such as for example chronic colitis (ulcerative colitis).

There is a particularly great need for suitable applications for the prevention or treatment of chronic inflammatory intestinal diseases, in particular chronic colitis (ulcerative colitis).

Chronic inflammation can appear as a cause of various diseases and living conditions. It can be associated with the most diverse conditions such as arthritis, some types of cancer, colitis, diabetes mellitus, coronary heart disease, obesity, Alzheimer's disease and immune dysfunction.

There are essentially two enzymatic pathways for regulating inflammation. The lipoxygenase pathway (5-LOX) results in the production of leukotrienes, which have a pro-inflammatory action. The second pathway is the cyclooxygenase pathway (COX-1 and COX-2). A high level of COX-2 indicates inflammation. Further inflammation markers are tumour necrosis factor (TNF-$\alpha$), nuclear factor $\kappa$B (NF-$\kappa$B), interleukin-6 (IL-6), interleukin-17 (IL-17) and interleukin-1-$\beta$ (IL1-$\beta$). The enzymes, cytokines and metabolites thereof increase the production of prostaglandins and leukotrienes, which function as intercellular mediators, and are connected with the inflammatory process. Regulation of the enzymes LOX-5 and COX-2 in particular can have a positive effect in the development/suppression of inflammation.

A diet which is based on much sugar and starch, and fat and trans fatty acids, has a direct connection with chronic inflammation. Oxidation of multiply unsaturated fats and fatty acids in vitro and in vivo leads to the formation of reactive oxygen species (radicals), and to the formation of nitrogen oxides. These compounds can initiate and/or promote the first phase of an inflammatory process. Damage to the DNA can result from this.

Over its whole length, particularly in the region of the intestine, the gastrointestinal tract is susceptible to inflammation, hence it is very important to inhibit corresponding processes and to prevent inflammation. Without treatment, harmful processes can lead to irritation, acute and chronic inflammation, and onwards to cancer.

Chronic inflammatory diseases of the digestive tract mucosa represent a considerable health political problem. Younger people in particular are falling ill, whose whole lifestyle is severely affected thereby, and who have to rely on medical care throughout their life. The aetiology/pathogenesis of the chronic inflammatory diseases of the digestive tract is not completely clear. However, it is believed to be a cause of the onset of a disorder of the intestinal barrier.

Ulcerative colitis and Crohn's disease are inflammations of the intestine, which exhibit characteristic accompanying symptoms such as diarrhoea, blood in stools, abdominal pains and cramps, and weight loss. At the same time, the intestinal mucosa appears red and swollen and often bleeds on the slightest touch.

The epithelial cells of the mucosa represent the cell layer closest to the surface. The intestinal epithelial cells constitute the greatest contact area of the body with the outside world. They absorb food and at the same time prevent the penetration of pathogenic organisms. The latter is promoted by chronic physiological inflammation. This is subject to a range of control and regulatory mechanisms in order to avoid on one hand the penetration of pathogenic germs and on the other hand damage due to the inflammatory mediators themselves. For this, the epithelial cells interact with the cells of the mucosa-associated immune system.

Intestinal epithelial cells possibly have an important role in the pathogenesis of chronic inflammatory intestinal diseases. The main model for the onset of chronic inflammatory intestinal diseases describes the following scenario: a defect in the structural integrity of the intestinal epithelium leads to an invasion of antigens from the intestinal lumen. In genetically predisposed patients, this process can trigger a chronic inflammation through activation of the mucosa-associated lymphatic tissue. A disorder of the cell-cell contact due to genetic modification of the N-adherin or keratin 8 triggers a chronic intestinal inflammation. Epithelial cells possess a large number of receptors for signal uptake. These in particular include receptors for the recognition of bacterial motifs, so-called pattern recognition receptors.

One such recognition receptor for bacterial motifs is the so-called NOD2/CARD15 protein. NOD2/CARD15 is a member of the NBS-LRR protein family (for nucleotide-binding site and leucine-rich repeat), the members whereof all play a part in the intracellular recognition of microbes and components thereof and which also include for example Apaf-1 and CARD4/NOD1, which possibly also can play a part in certain patients. When bacterial components bind to NOD2/CARD15, this normally leads to activation of the pro-inflammatory transcription factor NF-$\kappa$B.

Adherent *E. coli* strains have been found in ulcerations in patients with Crohn's disease. In general, in patients with IBD or IBS, considerably more bacteria are directly adjacent to the intestinal epithelial cells than in the normal mucosa, which is protected from contact with bacteria by a mucus layer. This observation supports the hypothesis of the importance of bacterial translocation in the pathogenesis of IBD.

The currently available therapies for the treatment of Crohn's disease and ulcerative colitis can alleviate, but not cure, the disease symptoms. Most therapies end with a resistance to the antibiotic and surgical intervention.

JP 2007/077122 describes the use of plant proanthocyanidins, for example from apple, pear, apricot, grape, guava, hops, barley or adzuki bean for the prevention of intestinal inflammation, especially in the case of ulcerative colitis. The recommended daily intake is 100 to 2500 mg apple extract or corresponding quantities of apple proanthocyanidins. The effect of the apple proanthocyanidins was confirmed in mice with acute ulcerative colitis caused by dextran sulphate (DSS, 2.5%) over a period of 20 days.

Models of the DSS-induced colitis (acute or chronic) are rapid, simple to perform, well reproducible and inexpensive. They enable the real-time study of the inflammatory process from onset up to remission and are thus very suitable for studies of epithelial regeneration and wound healing and for drug screening.

The S3 Guideline "Diagnosis and Therapy of Crohn's disease" summarizes the results (on the treatment of the aforesaid diseases) of an evidence-based consensus conference of the German Society for Digestive and Metabolic Diseases with the competence field Chronic inflammatory intestinal diseases (Z Gastroenterol 2008; 46: 1094-1146). For the therapy of such diseases, inter alia budesonide, systemically active steroids, sulfasalazine, azathioprine/6-mercaptopurine, methotrexate and anti-TNF-alpha antibodies have until now been used.

Overall, however, there is still a need for suitable uses for the prophylaxis and/or treatment of inflammation.

SUMMARY OF THE INVENTION

The primary purpose of the present invention was therefore to provide appropriate applications, in particular uses for the prophylaxis and/or treatment of one, several or preferably all of the diseases or symptoms described above. Further and especially preferred formulations of the present invention follow from the following description, the examples and the appended patent claims.

The primary purpose of the present invention is achieved by means of a compound of the formula (X)

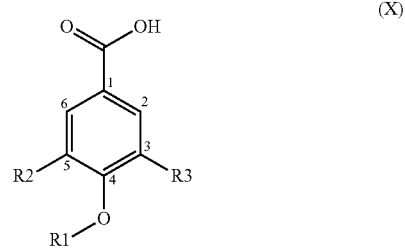

or
a salt of a compound of the formula (X)
or
a mixture containing or consisting of
two or more different compounds of the formula (X),
two or more different salts of compounds of the formula (X)
or
one or more different compounds of the formula (X) and one or more different salts of compounds of the formula (X), wherein for R1, R2 and R3 independently of one another in every compound of the formula (X), the following applies:
R1 means hydrogen or methyl,
R2 means an organic residue with 5 carbon atoms and one oxygen atom or none and
R3 means an organic residue with 10 carbon atoms and one or more, preferably one or two, oxygen atoms,
or
R1 and R2 together with the carbon atoms in positions 4 and 5 and the oxygen atom bound to the carbon atom in position 4 form a ring and comprise 5 carbon atoms and one oxygen atom or none, and
R3 means an organic residue with 10 carbon atoms and one or more, preferably one or two, oxygen atoms, for use in a method for the prophylaxis and/or treatment of inflammation, in particular of inflammation of the (human or animal) skin, in particular in a method for reducing the release of TNF-alpha, and/or
for reducing the release of an interleukin, preferably of IL-1, IL-6 and/or IL-8, and/or
for reducing the release of a prostaglandin, preferably of PGE2, and/or
for reducing the release of interferon-gamma and/or NF-κB,
particularly preferably in a method
for reducing the release of TNF-alpha, and/or
for reducing the release of an interleukin, preferably of IL-1, IL-6 and/or IL-8, and/or
for reducing the release of a prostaglandin, preferably of PGE2.

Essentially therefore, the present invention relates to the aforementioned compounds, salts or mixtures thereof as anti-inflammatory active substances.

For the term "skin", the aforesaid respectively applies. The skin to be treated according to the invention is thus preferably human or animal external skin (in the conventional sense) and/or a mucous membrane, in particular the oral mucosa, the gastric mucosa and/or the intestinal mucosa, in particular for the prophylaxis and/or treatment of one or more of the diseases or symptoms described above.

Preferably the method for the prophylaxis and/or treatment of inflammation is
(a) a method for the prophylaxis and/or treatment of chronic inflammatory diseases, in particular intestinal diseases,
and/or
(b) a method for strengthening damaged or undamaged skin, in particular mucosa,
and/or
(c) a method for reducing tissue damage, in particular tissue damage in the intestine,
and/or
(d) a method for recreating a normal cellular composition in the intestine,
and/or
(e) a method for recreating or stabilizing the function of skin, in particular of mucosa.

Particularly advantageous and therefore preferred according to the invention is a use as described above, wherein for the groups R1, R2 and R3 in the compound of the formula (X) or independently of one another in one, several or all, preferably all, compound(s) of the formula (X) the following applies:
R3 means

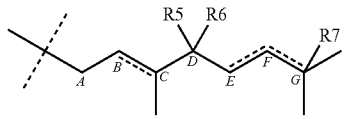

wherein
the dotted line which links the carbon atoms designated as B and C means that a single bond or a double bond is present between these carbon atoms, and
the dotted line which links the carbon atoms designated as E and G means an individual double bond, which is positioned either between the carbon atoms designated as F and G or between the carbon atoms designated as E and F,
R7, for the case where the double bond is positioned between the carbon atoms designated as E and F, means a hydroxy group or, for the case where the double bond is positioned between the carbon atoms designated as F and G, is absent,
R5 and R6 mean a hydrogen atom and a hydroxy group or together mean an oxygen atom,
the dashed line marks the bond which links R3 with the carbon atom in position 3;
R1 means hydrogen or methyl
and R2 means

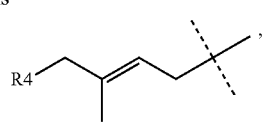

wherein R4 means hydrogen or a hydroxy group and the dashed line marks the bond which links R2 with the carbon atom in position 5
or
R1 and R2 together mean

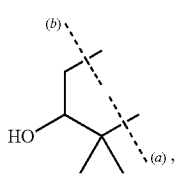

wherein the dashed line (a) marks the bond which links the tertiary carbon atom with the oxygen atom bound to the carbon atom in position 4 and the dashed line (b) marks the bond which links the secondary carbon atom with the carbon atom in position 5.

Particularly preferable is a use according to the invention (as described above), wherein one, several or all compound(s) of the formula (X) is selected or are each selected independently of one another from the group consisting of the following compounds (1) to (10):

(1)
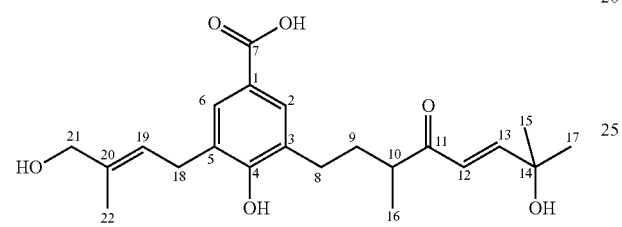
Erionic acid A (2)
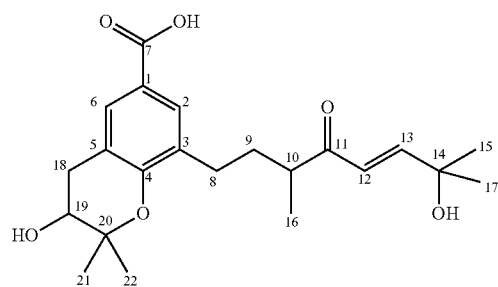
Erionic acid B (3)
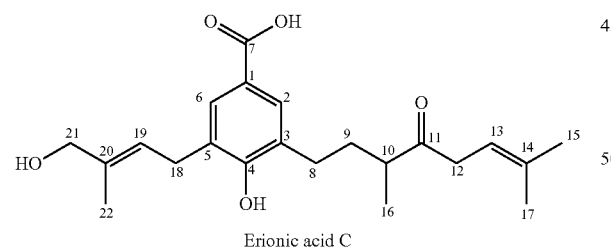
Erionic acid C (4)
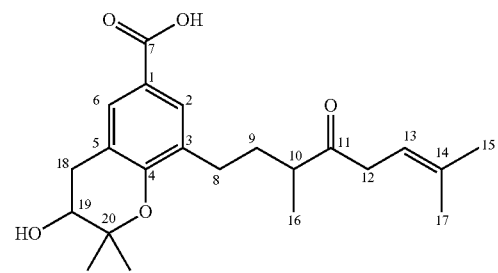
Erionic acid D (5)
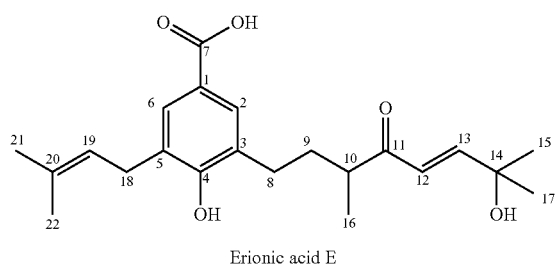
Erionic acid E (6)
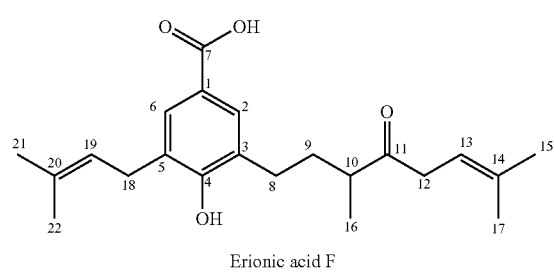
Erionic acid F (7)
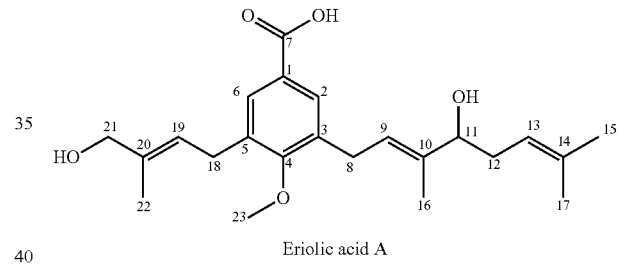
Eriolic acid A (8)
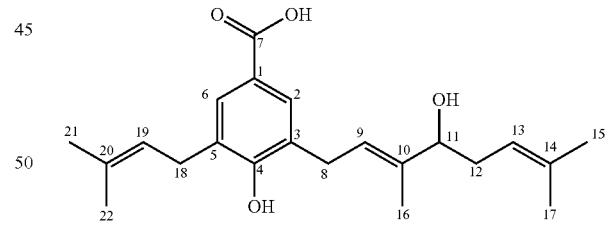
Eriolic acid B (9)
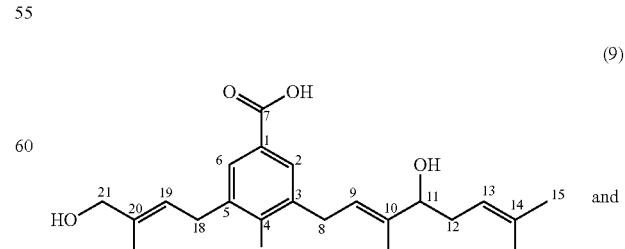
Eriolic acid C and

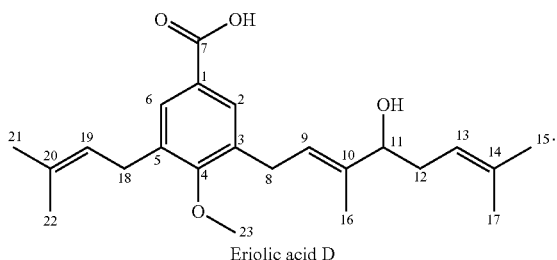

Eriolic acid D

Erionic acid A corresponds to: 4-hydroxy-3-((E)-7-hydroxy-3,7-dimethyl-4-oxo-oct-5-enyl)-5-((E)-4-hydroxy-3-methyl-but-2-enyl)-benzoic acid (1)

Erionic acid B corresponds to: 3-hydroxy-8-((E)-7-hydroxy-3,7-dimethyl-4-oxo-oct-5-enyl)-2,2-dimethyl-chroman-6-carboxylic acid (2)

Erionic acid C corresponds to: 3-(3,7-dimethyl-4-oxo-oct-6-enyl)-4-hydroxy-5-((E)-4-hydroxy-3-methyl-but-2-enyl)-benzoic acid (3)

Erionic acid D corresponds to: 8-((E)-3,7-dimethyl-4-oxo-oct-5-enyl)-3-hydroxy-2,2-dimethyl-chroman-6-carboxylic acid (4)

Erionic acid E corresponds to: 4-hydroxy-3-((E)-7-hydroxy-3,7-dimethyl-4-oxo-oct-5-enyl)-5-(3-methyl-but-2-enyl)-benzoic acid (5)

Erionic acid F corresponds to: 3-(3,7-dimethyl-4-oxo-oct-6-enyl)-4-hydroxy-5-(3-methyl-but-2-enyl)-benzoic acid (6)

Eriolic acid A corresponds to: 3-((E)-4-hydroxy-3,7-dimethyl-octa-2,6-dienyl)-5-((E)-4-hydroxy-3-methyl-but-2-enyl)-4-methoxy-benzoic acid (7)

Eriolic acid B corresponds to: 4-hydroxy-3-((E)-4-hydroxy-3,7-dimethyl-octa-2,6-dienyl)-5-(3-methyl-but-2-enyl)-benzoic acid (8)

Eriolic acid C corresponds to: 4-hydroxy-3-((E)-4-hydroxy-3,7-dimethyl-octa-2,6-dienyl)-5-((E)-4-hydroxy-3-methyl-but-2-enyl)-benzoic acid (9) and Eriolic acid D corresponds to: 3-((E)-4-hydroxy-3,7-dimethyl-octa-2,6-dienyl)-4-methoxy-5-(3-methyl-but-2-enyl)-benzoic acid (10).

The benzoic acids of the formula (X) to be used according to the invention can contain one or more asymmetric carbon atoms. These can each be present in the (R) or (S) configuration. These stereoisomers can be present as enantiomers, diastereomers or epimers, in particular as (R), (S), (R,R), (R,S), (S,R) or (S,S)-configured compounds or as any mixture of these compounds, for example as a racemate, or also as any mixture of the corresponding diastereomers.

Particularly preferable according to the invention is a mixture (as described above), containing or consisting of two or more different compounds of the formula (X), preferably of two, three, four, five, six, seven, eight, nine or ten different compounds of the formula (X), preferably selected from the group consisting of the compounds (1) to (10).

The aforementioned compounds (7) and (9) are two commercially available compounds (for example supplied by the firm Ambinter) identified in *Herba Santa*. However no references to an anti-inflammatory action of these compounds are known in the state of the art. It was particularly surprising that the compounds of the formula (X) from *Herba Santa* to be used according to the invention are particularly well suited for use as anti-inflammatory active substances.

*Herba Santa* (also *Yerba Santa*, mountain balm) in general designates *Eriodictyon* ssp., in particular *Eriodictyon californicum* (H. & A.) Torr and *Eriodictyon angustifolium* (from the Hydrophyllaceae family). *Herba Santa* foliage has already long been used as a medicinal plant on account of its medicinal action. Traditionally, the plants, which were originally found in Mexico and the west of the USA, were used by American indigenous inhabitants and later by Spanish settlers (Heinsen, 1972; Munz, 1973; Barrett and Gifford, 1933; Immel, 2006). The antibacterial action of extracts from *Eriodictyon californicum* was described by Salle et al. in 1951 (Arch. Biochem. Biophys. 1951, 32, 121-123). The main substances contained in *Eriodictyon* sp. include various flavanones, inter alia homoeriodictyol, hesperetin, sterubin, chrysoeriol and luteolin (Hadleyy and Gisvold, 1942; Ley et al., J. Agric. Food Chem., 2005). The different biological actions of *Herba Santa* were previously mainly attributed to the flavanones contained, the composition and structures whereof had already been studied. Scarcely anything is so far known in the literature concerning the properties of the components from *Herba Santa* which do not have a flavanoid structure. In particular, nothing is known concerning an anti-inflammatory action of the compounds to be used according to the invention. The compounds (1) to (10) also occurring in various *Eriodictyon* sp. were only recently described for the first time. Their capabilities as antioxidants are presented in DE 10 2009 020729 A1. However, nothing was hitherto known concerning (additional) anti-inflammatory properties.

Particularly preferable according to the invention is a mixture for use in a method for the prophylaxis and/or treatment of inflammation (as described above), comprising a compound of the formula (X), a salt of the formula (X) or a mixture thereof (as respectively described above) and additionally a hydroxyflavone of the formula (Y)

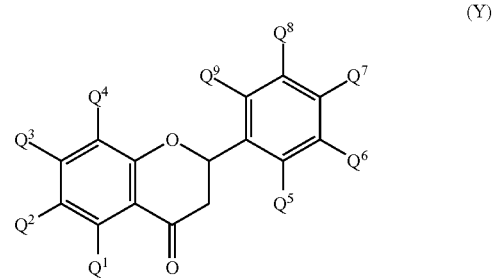

or a salt of a hydroxyflavone of the formula (Y)

or a mixture containing or consisting of two or more different hydroxyflavones of the formula (Y), two or more different salts of hydroxyflavones of the formula (Y) or one or more different hydroxyflavones of the formula (Y) and one or more different salts of hydroxyflavones of the formula (Y), wherein for Q1, Q2, Q3, Q4, Q5, Q6, Q7, Q8 and Q9 independently of one another in each hydroxyflavone of the formula (Y) the following applies:

Q1 to Q9 independently of one another mean hydrogen atoms, hydroxy groups, methyl, ethyl, 1-propyl, methoxy, ethoxy, 1-propyloxy or 2-propyloxy groups, with the proviso that at least one of the residues Q1 to Q9 represents a hydroxy group, and wherein preferably the following applies:

Q2, Q4, Q5, Q8 and Q9 represent hydrogen atoms,

Q1, Q3 and Q6 independently of one another mean hydrogen atoms, hydroxy or methoxy groups, with the proviso that at least one of the residues Q1 and Q3 represents a hydroxy group, and Q7 represents a hydroxy group.

The hydroxyflavones of the formula (Y) can be present as mono- or (in the case of several hydroxy groups) multivalent anions, wherein as counter-cations the singly positively charged cations of the first main and transition group, the ammonium ion, a trialkylammonium ion, the divalently charged cations of the second main and transition group, and the trivalent cations of the $3^{rd}$ main and transition group, preferably, $Na^+$, $K^+$, $NH_4^+$, $Ca^{2+}$, $Mg^{2+}$, $Al^{3+}$ and $Zn^{2+}$, are used.

The hydroxyflavones of the formula (Y) can be present as (2S) or (2R) enantiomers or as a mixture of both. Preferably the hydroxyflavones of the formula (Y) are present as the (2S) enantiomer or as a mixture enriched in (2S) enantiomer.

Without thereby limiting the invention, the following compounds may be mentioned by way of example: 2-(4-hydroxyphenyl)-5,7-dihydroxychroman-4-one (naringenin), 2-(3,4-dihydroxyphenyl)-5,7-dihydroxychroman-4-one (eriodictyol), 2-(3,4-dihydroxyphenyl)-5-hydroxy-7-methoxychroman-4-one (eriodictyol 7-methyl ether), 2-(3,4-dihydroxyphenyl)-7-hydroxy-5-methoxychroman-4-one (eriodictyol 5-methyl ether), 2-(4-hydroxy-3-methoxyphenyl)-5,7-dihydroxychroman-4-one (homoeriodictyol) and 2-(3-hydroxy-4-methoxyphenyl)-5,7-dihydroxychroman-4-one (hesperetin), (2S) or (2R) enantiomers thereof or mixtures thereof, and mono- or multivalent phenolate salts thereof with $Na^+$, $K^+$, $NH_4^+$, $Ca^{2+}$, $Mg^{2+}$ or $Al^{3+}$ as counter-cations.

The structures of preferred examples of hydroxyflavones of the formula (Y) are shown below (see compounds (11) to (16)):

(11)

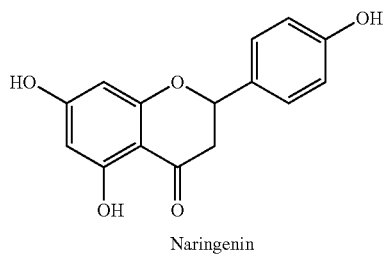

Naringenin (12)

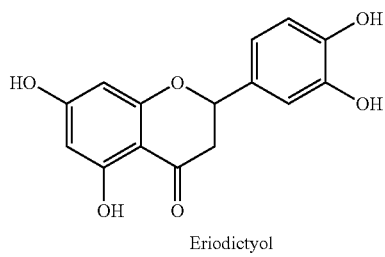

Eriodictyol (13)

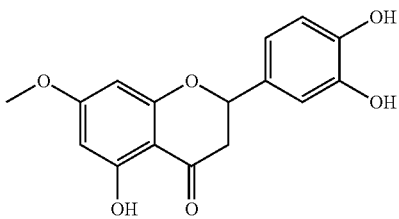

Eriodictyol-7-methyl ether (14)

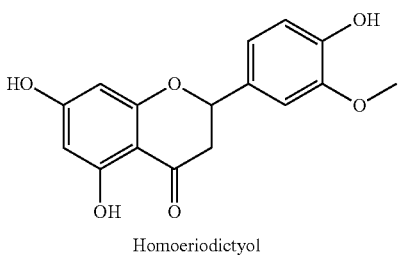

Homoeriodictyol (15)

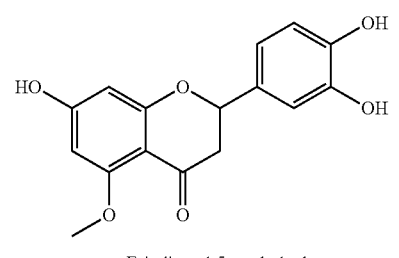

Eriodictyol-5-methyl ether (16)

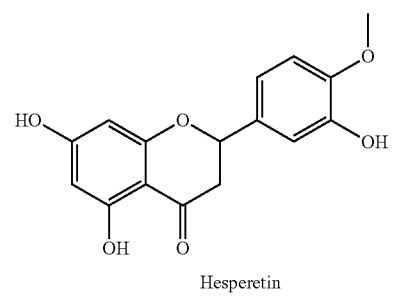

Hesperetin

Particularly preferable is a mixture (as described above) comprising one, several or all compounds of the formula (Y) selected from the group consisting of homoeriodictyol, sterubin, eriodictyol, hesperetin, chrysoeriol and luteolin.

Particularly preferably, such a mixture contains at least homoeriodictyol as a compound of the formula (Y).

According to a preferable embodiment of the present invention, a mixture (as described above) is provided for the use, wherein the proportion of the total quantity of compounds of the formula (X) and salts of compounds of the formula (X) in the mixture, based on the total weight of the mixture, is 1 to 99 wt. %, preferably 10 to 99 wt. %, particularly preferably 20 to 80 wt. %, and/or the proportion of the total quantity of compounds of the formula (Y) and salts of compounds of the formula (Y) in the mixture, based on the total weight of the mixture, is 1 to 99 wt. %, preferably 10 to 99 wt. %, particularly preferably 20 to 80 wt. %, wherein preferably the proportion of the total quantity of compounds of the formula (X), compounds of the formula (Y), salts of compounds of the formula (X) and salts of compounds of the formula (Y) in the mixture, based on the total weight of the mixture, is 0.0001 to 100 wt. %, preferably 0.001 to 100 wt. %, particularly preferably 0.1 to 90 wt. %, more preferably 1 to 90 wt. %. According to an especially preferred embodiment, the proportion is 10 to 90 wt. %, in particular 25 to 90 wt. % (preferably up to 100 wt. %), more preferably 45 to 90 wt. % (preferably up to 100 wt. %).

Surprisingly, in our own studies it was found that certain extracts prepared from *Herba Santa* foliage or fractions therefrom are particularly suitable for treating inflammatory processes, for example with inflammation in the gastrointestinal tract or gingivitis, and/or preventing these. Hence, according to a further aspect of the present invention, a mixture is stated for the use described according to the invention, wherein the mixture comprises a plant extract or consists thereof, preferably an extract from *Eriodictyon* ssp., particularly preferably an extract from *Eriodictyon californicum* and/or *Eriodictyon angustifolium*, wherein the proportion of the total quantity of compounds of the formula (X) and salts of compounds of the formula (X) in the mixture, based on the total weight of the mixture, is preferably 0.1 to 100 wt. %, more preferably 1 to 100 wt. %, particularly preferably 10 to 100 wt. %, and more preferably from 10 to 90 wt. %.

Particularly preferably, the ratio of the total quantity of compounds of the formula (X) and salts of compounds of the formula (X) to the total quantity of compounds of the formula (Y) and salts of compounds of the formula (Y) in a mixture described herein usable according to the invention lies in the range from 0.00001:1 to 1:0.00001, in particular in the range from 0.0001:1 to 1:0.0001, preferably in the range from 0.001:1 to 1:0.001, preferably in the range from 0.01:1 to 1:0.01, particularly preferably in the range from 0.1:1 to 1:0.1, and more preferably in the range from 0.5:1 to 1:0.5, each based on the weight.

According to a preferable embodiment of the present invention, a mixture described herein comprises as compounds of the formula (Y) homoeriodictyol and sterubin or salt(s) thereof. Here, as regards preferable quantity data and ratios, the aforesaid respectively applies.

In a preferable embodiment of such a mixture, the mixture contains a total quantity of homoeriodictyol and sterubin (and/or salts thereof) which is greater than the total quantity of compounds of the formula (X) (and optionally salts thereof).

The present invention also relates to preparations, in particular preparations used for food or enjoyment, pharmaceutical preparations, cosmetic preparations or dermatological preparations for use in a method for the prophylaxis and/or treatment of inflammation, comprising a compound, a salt or a mixture as defined above, for use in a method for the prophylaxis and/or treatment of inflammation.

Preferably these are preparations for the prophylaxis and/or treatment of inflammation of the skin (as described above), in particular in a method
 for reducing the release of TNF-alpha, and/or
 for reducing the release of an interleukin, preferably of IL-1, IL-6 and/or IL-8, and/or
 for reducing the release of a prostaglandin, preferably of PGE2, and/or
 for reducing the release of interferon-gamma and/or NF-κB,
 particularly preferably in a method
 for reducing the release of TNF-alpha, and/or
 for reducing the release of an interleukin, preferably of IL-1, IL-6 and/or IL-8, and/or
 for reducing the release of a prostaglandin, preferably of PGE2.

Preferably here this is also
(a) a method for the prophylaxis and/or treatment of chronic inflammatory diseases, in particular intestinal diseases,
and/or
(b) a method for strengthening damaged or undamaged skin, in particular mucosa,
and/or
(c) a method for reducing tissue damage, in particular tissue damage in the intestine,
and/or
(d) a method for recreating a normal cellular composition in the intestine, and/or
(e) a method for recreating or stabilizing the function of skin, in particular of mucosa.

Moreover, the aforesaid also respectively applies, in particular as regards the contained compounds of the formula (X) or salts thereof and the optionally contained compounds of the formula (Y) or salts thereof.

Preferably a preparation described above contains a mixture preferred according to the invention (as described above).

A mixture according to the invention or a mixture usable according to the invention, preferably a mixture described above as preferable, is preferably producible by a method with the following steps:
(a) Extraction of plant material from *Eriodictyon* ssp., preferably from *Eriodictyon californicum* and/or *Eriodictyon angustifolium*, so that a mixture is formed which contains compounds of the formula (X), optionally compounds of the formula (Y) and other extracted compounds, and
(b) Concentration of extracted compounds of the formula (X) and/or salts of the extracted compounds of the formula (X) and optionally compounds of the formula (Y) and/or salts of the extracted compounds of the formula (Y) in the mixture by partial or complete removal of other extracted compounds and optionally removal of extractants and/or solvents,
preferably so that the proportion of the total quantity of compounds of the formula (X) and salts of compounds of the formula (X) in the mixture based on the total weight of the mixture is 0.1 to 100 wt. %, more preferably 1 to 100 wt. %, particularly preferably 10 to 100 wt. %, more preferably from 10 to 90 wt. %.

Preferably the plant material here is selected from the group consisting of:
*Eriodictyon altissimum* P. V. Wells—Indian Knob mountain balm
*Eriodictyon angustifolium* Nutt. —Narrow-leaved *Yerba Santa*
*Eriodictyon californicum* (Hook. & Arn.) Torr.—California *Yerba Santa*
*Eriodictyon capitatum* Eastw. —Lompoc *Yerba Santa*
*Eriodictyon crassifolium* Benth. —Thick-Leaved *Yerba Santa*
*Eriodictyon tomentosum* Benth
*Eriodictyon traskiae* and
*Eriodictyon trichocalyx* (Syn.: *Eriodictyon lanatum* (Brand) Abrams)—Hairy *Yerba Santa*

According to a preferable aspect of the present invention, a mixture described herein or a preparation described herein comprises or consists of an appropriately concentrated extract from *Herba santa*, preferably from plant material as described above.

In the context of the present invention, an extract from fresh or dried *Herba Santa* plants or plant parts is preferable, particularly preferably from plants or plant parts with a solids content of 90 wt. % or more. Particularly preferably, the extract is from above-ground plant parts, in particular from leaves, buds, stems, bark, flowers and/or fruit of *E. angustifolium* or *E. californicum*.

Extracts from *Herba Santa* foliage (as described above) can be obtained by extraction methods known per se from the fresh or dried foliage of the plants. These for example include maceration or percolation. As the extraction medium, for example water and ethanol or mixtures thereof can be used. Instead of ethanol, methanol and other water-soluble solvents can also be used. Likewise, ethyl acetate can be used as a solvent. Selection of the temperature and mechanical disintegration of the fruit can promote the extraction. According to the state of the art, the mechanical disintegration of the dried foliage e.g. with stirrers, homogenizers or ultrasound is also advisable. Further, other extraction-promoting substances, such as acids, bases and enzymes, can be used.

In the context of the present text, the term "*Herba Santa* foliage" in particular comprises leaves, buds, bark, flowers, fruit and stems of *Eriodictyon angustifolium, E. californicum, E. trichocalyx, E. traskiae,* and *E. crassifolium*.

BRIEF DESCRIPTION OF THE DRAWINGS

The identification and quantification of flavones and bisprenylated benzoic acid derivatives in different *Eriodictyon* sp. can be effected by means of RP-HPLC-UV/Vis and RP-HPLC-MS/MS after the methanolic extraction, as performed in the context of our own studies. The flavonoid contents, or contents of bisprenylated benzoic acid derivatives can be determined by means of external calibration with use of standard substances. The appended FIGS. 1 *a* and 1 *b* respectively show by way of example the flavonoid or erionic/eriolic acid profile of extracts studied (FIG. 1*a*: LC-MS chromatogram of the flavonoid fraction from *Eriodictyon angustifolium* extract.

DESCRIPTION OF THE PREFERRED EMBODIMENTS

Figure 1A:
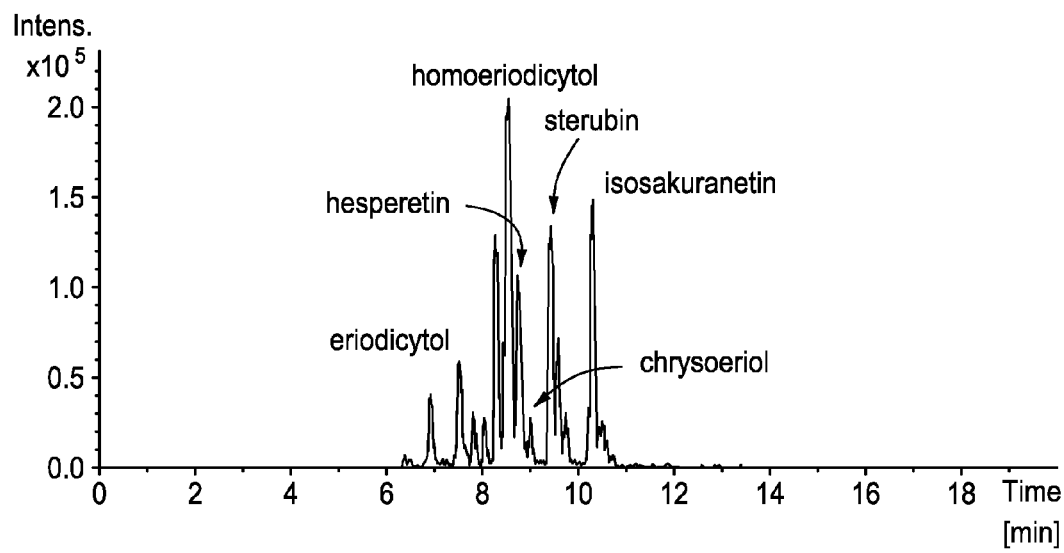
FIG. 1*b*: LC-MS chromatogram of the erionic acid fraction from *Eriodictyon angustifolium* extract; each after fractionation over Sephadex LH-20).
Figure 1B:
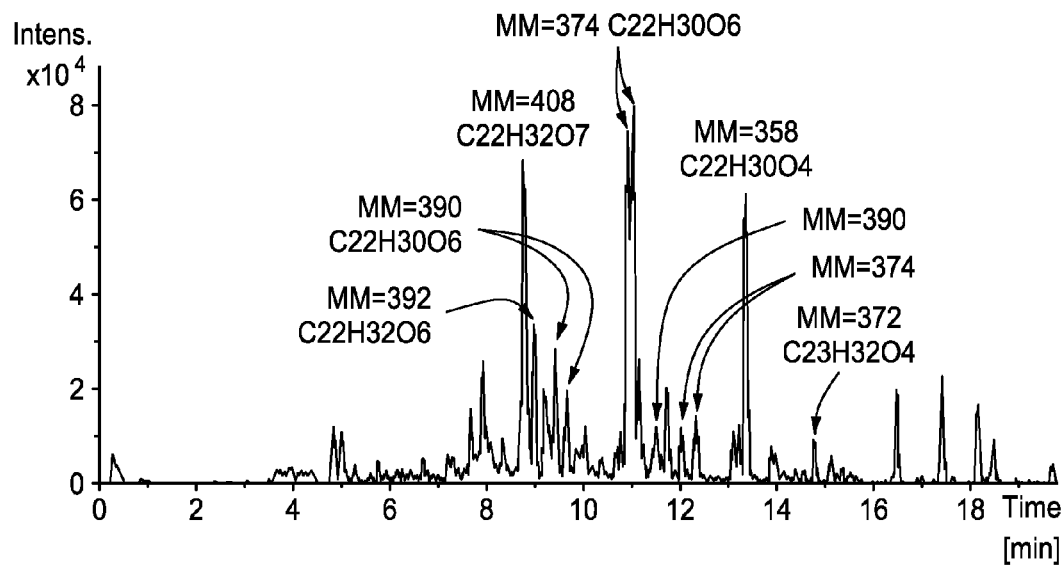

In the light of the above explanations, a preparation according to the invention or a mixture according to the invention (as respectively described above) preferably comprises or consists of (i) *Herba Santa* foliage, (ii) an optionally concentrated extract prepared therefrom or (iii) a fraction thereof.

In the mixtures or preparations according to the invention, as well as the components described above, one or more further substances can be contained. Preferably one or more (further) substances which are suitable for influencing inflammatory states of the skin, in particular for prophylactic and/or therapeutic uses as described above, are contained. Furthermore, one or more substances for the treatment of a deficiency phenomenon arising during inflammation of the skin (in particular a deficiency of potassium, sodium, iron, calcium, vitamin D and/or folic acid) can be contained.

In the mixtures or preparations according to the invention, one or more further components selected from the following group are preferably (also) contained: probiotic bacteria (e.g. lactobacilli, bifidobacteria and enterococci), prebiotics (e.g. inulin and fructooligosaccharides), synbiotics (pro- and pre-biotics), ballast substances (e.g. cellulose, starch, resistant starch and fibres, such as for example apple fibres), whey proteins, soya proteins, minerals (in particular Ca, Mg, with a combination of Ca, Mg and inulin being particularly preferable), tocopherols (e.g. vitamin E, vitamin E acetate), vanilla, vanilla extracts, omega-3 fatty acids (preferably fish oil), citrus, apple, grape seed, green tea, rosemary, tarragon, thyme, horseradish and mace extracts, tannins, tomato, melon and rose hip extracts (in particular lycopene-containing extracts), beta-carotene; aubergines, rhubarb, red onions, red cabbage, black carrot, superfruits, in particular açai, noni, goji, pomegranate, mangosteen, currrants, strawberries, aronia, blueberries and/or elderberries, preferably in the form of dried fruit, extracts or fruit preparations; soya isoflavones, nonsteroidal antiinflammatory drugs, antibiotics, budesonide, systemically active steroids, sulfasalazine, azathioprine/6-mercaptopurine, methotrexate, anti-TNF-alpha antibodies, bisabolol, sodium laurylsulphate, chlorhexidine, metal fluorides (e.g. aluminium and tin fluoride), organic and inorganic fluorides, flavourings, essential oils, cooling active substances, in particular menthol, extracts or pure substances from eucalyptus, thyme, wintergreen, spearmint and peppermint.

Preparations according to the invention (in particular the preparations designated above as preferable) are preferably selected from the group consisting of:

fruit juice-containing drinks; vegetable juice-containing drinks; bakery products; confectionery; snacks; instant products; soups; sauces; spice mixtures; ice cream; fruit preparations; desserts; dairy products; soya products; cereals; food supplements, medicinal products and pharmaceutical products.

Fruit juice-containing drinks here are in particular fruit juices and smoothies (whole fruit drinks). Vegetable juice-containing drinks are in particular juices of red beet and black carrot.

Bakery products are in particular cakes, waffles and biscuits.

Confectionery is in particular lozenges and chewing gums, fruit gums, chewing sweets, (breath freshening) sweets, boiled sweets, hard caramels, chocolate creams, sweets and chocolate.

Instant products are in particular instant meals and other instant products, e.g. drink powders and granules.

Fruit preparations are in particular jams, preserves and fruit sauces.

Desserts are in particular puddings and jellies.

Dairy products comprise in particular quark, yoghurt, milk drinks and whey preparations.

Cereals are in particular cornflakes, muesli and muesli bars.

Further preferable preparations, in particular food supplements, medicinal products and pharmaceutical products, are
solid galenical forms (such as for example tablets (with and without coating, with and without modified release), sugar-coated tablets (with and without coating, with and without modified release), capsules (soft or hard gelatine capsules with and without modified release) granules (with and without modified release), powders (with and without modified release), suppositories (with and without coating, with and without modified release), lozenges and chewing gums), liquid forms (such as for example solutions, suspensions, emulsions, syrups (colloquially cough syrup), mouthwashes, gargle solutions, throat sprays or nasal sprays, nasal drops, nasal rinse solutions, nasal powders, nasal ointments or ear drops, ear sprays, ear rinse solutions, ear powders and aural tampons), semisolid forms (such as for example hydrophobic ointments including for example: hydrocarbon gels, lipogels, silicone gels, oleogels and water-absorbing ointments including for example absorption bases, hydrophilic ointments, hydrophilic gels (hydrogels) or pastes, Inhalants (such as for example compressed gas dispenser inhalers, powder inhalers, inhalers with atomisers, and inhalation concentrates for inhalation), active substance-containing plasters or other therapeutic systems and cosmetic and/or dermatological preparations, which (except for the substances to be used according to the invention) are constituted as usual and are used for cosmetic, in particular dermatological sun protection, for the treatment, care and cleansing of the skin and/or the hair or as a make-up product in decorative cosmetics. Accordingly, such preparations can be present as for example cleaning agents such as for example soap, syndet, liquid wash, shower and bath preparation, skin care agents such as for example emulsion (as solution, dispersion, suspension; cream, lotion or milk depending on production method and ingredients of the type W/O, O/W or multiple emulsion, PIT emulsion, emulsion foam, micro- or nanoemulsion, Pickering emulsion), ointment, paste, gel (including hydro-, hydrodispersion- and oleogel), alcoholic or aqueous/alcoholic solution, oil, toner, balsam, serum, powder, wipe, Eau de Toilette, Eau de Cologne, perfume, wax, including the presentation as stick, roll-on, (pump-)spray, aerosol (foaming, non-foaming or after-foaming), skin care products (as described above), as foot care products (including keratolytic agents and deodorants), as insect repellents, as sunscreen agents, as self-tanning agents and/or aftersun preparations, skin care products as shaving products or aftershave, as depilatory agents, as hair care products such as for example shampoo (including shampoo for normal hair, for greasy hair, for dry, stressed (damaged) hair, 2-in-1 shampoo, antidandruff shampoo, baby shampoo, shampoo for dry scalp, shampoo concentrate), conditioner, hair mask, hair lotion, hair conditioner, hair cream, pomade, permanent wave and fixing agents, hair straighteners (straighteners, relaxers), hair setting lotions, styling aids (e.g. gel or wax); bleaching agents, hair dyes such as for example temporary, direct and semipermanent hair dyes, permanent hair dyes), skin care products as decorative toiletry products, such as for example nail care products (nail varnish and nail varnish remover), decorative cosmetics (e.g. powder, eyeshadow, eye pencil, lipstick), skin care products as deodorant and/or antiperspirant; mouthwash and oral waterjet, and oral care products (e.g. toothpaste, tooth cream, tooth gel, tooth powder, tooth cleaning fluid or foam, mouthwash, tooth cream and mouthwash as 2-in-1 product, mouth spray, dental floss or dental care chewing gum). Such oral or dental care products as a rule contain abrasive systems (abrasive or polishing ingredients), such as silicates, calcium carbonate, calcium phosphate, aluminium oxide and/or hydroxyapatite, surfactant substances, e.g. sodium laurylsulphate, sodium laurylsarcosinate and/or cocamidopropyl betaine, humectants such as glycerol and/or sorbitol, thickeners, e.g. carboxymethyl-celluloses, polyethylene glycols, carrageenan and/or Laponite®, sweeteners such as saccharin, flavour/taste correctants for unpleasant taste sensations, taste-modulating substances (e.g. inositol phosphate, nucleotides, e.g. guanosine monophosphate, adenosine monophosphate or other substances, e.g. sodium glutamate or 2-phenoxypropionic acid), cooling active substances, e.g. menthol derivatives (e.g. L-menthyl lactate, L-menthyl alkyl carbonates, menthone ketals), icilin and icilin derivatives, stabilizers and active substances, e.g. sodium fluoride, sodium monofluorophosphate, tin difluoride, quaternary ammonium fluorides, zinc citrate, zinc sulphate, tin pyrophosphate, tin dichloride, mixtures of various pyrophosphates, triclosan, cetylpyridinium chloride, aluminium lactate, potassium citrate, potassium nitrate, potassium chloride, strontium chloride, hydrogen peroxide, flavourings, sodium bicarbonate and/or odour correctants, and chewing gums or dental care gums consisting of a chewing gum base containing elastomers, e.g. polyvinyl acetates (PVA), polyethylenes, (low or medium molecular weight) polyisobutenes (PIB), polybutadienes, isobutene-isoprene copolymers, polyvinyl ethyl ethers (PVE), polyvinyl butyl ethers, copolymers of vinyl esters and vinyl ethers, styrene/butadiene copolymers (SBR) or vinyl elastomers, e.g. based on vinyl acetate/vinyl laurate, vinyl acetate/vinyl stearate or ethylene/vinyl acetate, and mixtures of the said elastomers such as for example described in EP 0 242 325, U.S. Pat. No. 4,518,615, U.S. Pat. No. 5,093,136, U.S. Pat. No. 5,266,336 U.S. Pat. No. 5,601,858 or U.S. Pat. No. 6,986,709. In addition, chewing gum bases contain further ingredients, e.g. (mineral) fillers (e.g. calcium carbonate, titanium dioxide, silicon dioxide, talc, aluminium oxide, dicalcium phosphate, tricalcium phosphate, magnesium hydroxide and mixtures thereof, plasticizers (e.g. lanolin, stearic acid, sodium stearate, ethyl acetate, diacetin (glycerol diacetate), triacetin (glycerol triacetate) and triethyl citrate), emulsifiers (e.g. phosphatides, such as lecithin and mono and diglycerides of fatty acids, e.g. glycerol monostearate), antioxidants, waxes (e.g. paraffin waxes, candelilla waxes, carnauba wax, microcrystalline waxes and polyethylene waxes), fats or fatty oils (e.g. hardened (hydrogenated) plant or animal fats) and mono, di- or triglycerides.

Preferable preparations according to the invention used for food or enjoyment are:

Confectionery such as for example lozenges and chewing gums, fruit gums, chewing sweets, (breath freshening) sweets, boiled sweets, hard caramels, chocolate creams, sweets and chocolate, bakery products such as cakes, waffles and biscuits, snacks, instant meals and other instant products (drink powders and granules), ice cream, fruit preparations (jams, preserves and fruit sauces), desserts (puddings, jellies), dairy products (quark, yoghurts, probiotic yoghurts, milk drinks, whey preparations) and cereals (cornflakes, muesli and muesli bars).

Especially preferred preparations according to the invention used for food or enjoyment are fruit gums, fruit preparations (jams, preserves and fruit sauces), dairy products (quark, yoghurts, probiotic yoghurts, milk drinks, whey preparations) and cereals (cornflakes, muesli and muesli bars), wherein in turn the dairy products yoghurts, probiotic yoghurts and milk drinks are most preferred.

As further components for preparations according to the invention used in particular for food or enjoyment, normal primary, auxiliary and additive substances for food or luxury consumables can be used, e.g. water, mixtures of fresh or processed, plant or animal primary or raw substances (e.g. raw, roast, dried, fermented, smoked and/or boiled meat, bones, cartilage, fish, vegetables, fruit, spices, nuts, vegetable or fruit juices or pastes or mixtures thereof), digestible or non-digestible carbohydrates (e.g. amylose, amylopectin, inulin, xylans, cellulose), natural or hardened fats (e.g. tallow, lard, palm fat, coconut fat, hardened plant fat), oils (e.g. sunflower oil, peanut oil, maize oil, olive oil, fish oil, soya oil, sesame oil), fatty acids or salts thereof (e.g. potassium stearate), proteinogenic or non-proteinogenic amino acids and related compounds (e.g. γ-amino-butyric acid, taurine), peptides (e.g. glutathione), native or processed proteins (e.g. gelatine), enzymes (e.g. peptidases), nucleic acids, nucleotides, taste correctants for unpleasant taste sensations, further taste modulators for further, as a rule not unpleasant taste sensations, other taste-modulating substances (e.g. inositol phosphate, nucleotides such as guanosine monophosphate, adenosine monophosphate or other substances such as sodium glutamate or 2-phenoxypropionic acid), emulsifiers (e.g. lecithins, diacylglycerols, gum Arabic), stabilizers (e.g. carrageenan, alginate), preservatives (e.g. benzoic acid, sorbic acid), antioxidants (e.g. tocopherol, ascorbic acid), chelators (e.g. citric acid), organic or inorganic acidulants (e.g. malic acid, acetic acid, citric acid, tartaric acid, phosphoric acid), bitter substances (e.g. quinine, caffeine, limonin, amarogentin, humolone, lupolone, catechins, tannins), mineral salts (e.g. sodium chloride, potassium chloride, magnesium chloride, sodium phosphate), substances preventing enzymatic browning (e.g. sulphite, ascorbic acid), essential oils, plant extracts, natural or synthetic dyes or pigments (e.g. carotenoids, flavonoids, anthocyans, chlorophyll and derivatives thereof), spices, trigeminally active substances or plant extracts, containing such trigeminally active substances, cooling active substances such as for example menthol, menthol derivatives (e.g. L-menthol, L-menthyl lactate, L-menthyl glutarate, L-menthyl succinate) or cubebol, synthetic, natural or nature-identical flavourings or aromatic substances and odour correctants.

Preparations according to the invention, used in particular for food or enjoyment can additionally contain one or more taste correctants, preferably selected from the following list: nucleotides (e.g. adenosine 5'-monophosphate, cytidine 5'-monophosphate) or pharmaceutically acceptable salts thereof, lactisols, sodium salts (e.g. sodium chloride, sodium lactate, sodium citrate, sodium acetate, sodium gluconate), further hydroxy-flavanones (e.g. eriodictyol, homoeriodictyol or sodium salts thereof), in particular according to US 2002/0188019, hydroxybenzamides as per DE 10 2004 041 496 (e.g. 2,4-dihydroxybenzoic acid vanillylamide, 2,4-dihydroxybenzoic acid N-(4-hydroxy-3-methoxybenzyl)amide, 2,4,6-trihydroxybenzoic acid N-(4-hydroxy-3-methoxybenzyl)-amide, 2-hydroxybenzoic acid N-4-(hydroxy-3-methoxybenzyl)amide, 4-hydroxybenzoic acid N-(4-hydroxy-3-methoxybenzyl)amide, 2,4-dihydroxybenzoic acid N-(4-hydroxy-3-methoxybenzyl)amide monosodium salt, 2,4-dihydroxybenzoic acid N-2-(4-hydroxy-3-methoxyphenyl) ethylamide, 2,4-dihydroxybenzoic acid N-(4-hydroxy-3-ethoxybenzyl)-amide, 2,4-dihydroxybenzoic acid N-(3,4-dihydroxybenzyl)amide and 2-hydroxy-5-methoxy-N-[2-(4-hydroxy-3-methoxyphenyl)ethyl]amide (aduncamide), 4-hydroxybenzoic acid vanillylamide), bitter-masking hydroxydeoxybenzoins according to WO 2006/106023 and the documents based thereon (Symrise) (e.g. 2-(4-hydroxy-3-methoxyphenyl)-1-(2,4,6-trihydroxyphenyl)ethanone, 1-(2,4-dihydroxyphenyl)-2-(4-hydroxy-3-methoxy-phenyl) ethanone, 1-(2-hydroxy-4-methoxyphenyl)-2-(4-hydroxy-3-methoxyphenyl)-ethanone), amino acids (e.g. gamma-aminobutyric acid as per WO 2005/096841 for reduction or masking of an unpleasant taste sensation such as bitterness), malic acid glycosides as per WO 2006/003107, salty-tasting mixtures as per WO 2007/045566, diacetyl trimers as per WO 2006/058893, divanillin, mixtures of whey proteins with lecithins and/or bitter-masking substances such as gingerdiones according to WO 2007/003527.

Preparations according to the invention used in particular for food or enjoyment can additionally contain one or more alkamides, preferably selected from the group consisting of: 2E,4E-decadienoic acid N-isobutylamide (pellitorin), 2E,4Z-decadienoic acid N-isobutylamide (cis-pellitorin), 2Z,4Z-decadienoic acid N-isobutylamide, 2Z,4E-decadienoic acid N-isobutylamide, 2E,4E-decadienoic acid N-([2S]-2-methylbutyl)amide, 2E,4E-decadienoic acid N-([2S]-2-methylbutyl)amide, 2E,4E-decadienoic acid N-([2R]-2-methylbutylamide), 2E,4Z-decadienoic acid N-(2-methylbutyl)amide, 2E,4E-decadienoic acid N-piperide (achilleamide), 2E,4E-decadienoic acid N-piperide (sarmentin), 2E-decenoic acid N-isobutylamide, 3E-decenoic acid N-isobutylamide, 3E-nonenoic acid N-isobutylamide, 2E,6Z,8E-decatrienoic acid N-isobutylamide (spilanthol), 2E,6Z,8E-decatrienoic acid N-([2S]-2-methylbutyl)amide (homospilanthol), 2E,6Z,8E-decatrienoic acid N-([2R]-2-methylbutyl)amide, 2E-decen-4-ynic acid N-isobutylamide, 2Z-decen-4-ynic acid N-isobutylamide, sanshoole.

Preparations according to the invention, used in particular for prophylaxis and supplementation of food and for the therapy of disease states and for toiletries can preferably contain substances or combinations of substances from the following groups.

Fillers (e.g. cellulose, calcium carbonate), free-flow and anticaking agents (e.g. talc, magnesium stearate), coatings (e.g. polyvinyl acetate phthalate, hydroxypropyl-methylcellulose phthalate), disintegrants (e.g. starch, crosslinked polyvinylpyrrolidone), plasticizers (e.g. triethyl citrate, dibutyl phthalate) substances for granulation (lactose, gelatine), retardation (e.g. poly(meth)acrylic acid methyl/ethyl/2-trimethylaminoethyl ester copolymers in dispersion, vinyl acetate/crotonic acid copolymers) and compacting (e.g. microcrystalline cellulose, lactose), solvent, suspension or dispersion agents (e.g. water, ethanol), emulsifiers (e.g. cetyl alcohol, lecithin), substances for modification of the rheological properties (silicon dioxide, sodium alginate), substances for microbial stabilization (e.g. benzalkonium chloride, potassium sorbate), preservatives and antioxidants (e.g. DL-alpha-tocopherol, ascorbic acid), substances for modification of the pH (lactic acid, citric acid), propellant or inert gases (e.g. fluorinated chlorohydrocarbons, carbon dioxide), colorants (iron oxides, titanium dioxide), ointment bases (e.g. paraffins, beeswax), inter alia as described in the technical literature (e.g. Schmidt, Christin. Active and Auxiliary Substances for Individual and Bulk Formulation, and Large-scale Manufacture. 1999; Wissenschaftliche Verlagsgesellschaft mbH Stuttgart or Bauer, Frömming Führer. Textbook of Pharmaceutical Technology. 8$^{th}$ Edition, 2006. Wissenschaftliche Verlagsgesellschaft mbH Stuttgart).

Depending on the embodiment according to the invention and desired purpose, mixtures according to the invention (as described above) can also contain one or more of the components mentioned above in connection with preparations according to the invention.

A further aspect of the present invention relates to a compound, a salt, a mixture or a preparation, as respectively described or defined above, for use in a method for the treatment of animal or human skin which requires treatment with anti-inflammatory active substances. Regarding the selection of the compounds or the salts and the preferable composition of the mixtures and preparations, the aforesaid respectively applies.

The compounds (1) to (16) described herein advantageously possess a particularly strong anti-inflammatory action. The compounds (1) to (16) are advantageously suitable for supporting the natural defence mechanisms against inflammatory processes in physiological systems (of people and animals). Further, these compounds advantageously occur in plants with a long edible consumption history (e.g. *Herba Santa*) owing to which they are particularly suitable for use in foods.

Particularly advantageous according to the invention therefore is a mixture or a preparation as described above, where this comprises one, two, three, four, five, six, seven, eight, nine or all compounds (1) to (10) and also one, two, three, four, five or all compounds (11) to (16) or consists thereof. Particularly preferable here is a mixture or a preparation, which comprises all of the compound (1) to (16) or consists thereof.

Such a mixture or preparation wherein one, several or all compounds of the group of the compounds (1) to (16) are components of a plant extract, preferably an extract from *eriodictyon* ssp., particularly preferably an extract from *eriodictyon californicum* and/or *eriodictyon angustifolium*, is particularly preferable.

It was particularly surprising that the compounds of the formula (X) to be used according to the invention or salts thereof can mediate or possess strong anti-inflammatory effects. Compounds, salts, mixtures and preparations according to the invention (as respectively described above) are advantageously capable of positively influencing inflammatory parameters in monocytes. In cell models wherein irritated and inflammatory phenomena of the mucous membranes, especially of gingiva and the gastrointestinal tract, are simulated, these exhibit an anti-inflammatory action. In particular, the following inflammatory parameters are positively influenced according to the invention: PGE2, IL-1, TNF, IL-6 and IL 8, in particular PGE2. Appropriate experiments on this were performed as described in TS1 (see below, "Example TS: Test study"). Thus for example from a concentration of 1 μg/ml, eriol-/erion-containing fractions already exhibit a highly significant action on some of the abovementioned parameters. Concentrations of 10 μg/ml and more are particularly suitable. A total extract from *Herba Santa* foliage which contains compounds usable according to the invention or individual extracts therefrom for example exhibits significant effects on individual parameters from a concentration of 1 μg/ml and highly significant effects up to 250 μg/ml.

For salts of compounds of the formula (X) usable according to the invention, that stated further above respectively applies as regards the preferable meanings of the residues. The carboxylic acid group which is bound to the carbon atom in position 1 (according to the numbering shown in formula (X)) is then present deprotonated. In addition, one or more hydroxy groups (if present) are optionally also present deprotonated. Here, as well as the deprotonated compound(s) of the formula (X), a corresponding quantity of counter-cations are present, where these are preferably selected from the group consisting of: singly positively charged cations of the first main and transition group, ammonium ions, trialkylammonium ions, doubly positively charged cations of the second main and transition group and triply positively charged cations of the third main and transition group, and mixtures thereof. The maximum degree of deprotonation of a compound of the formula (X) on which such as salt is based is found from the carboxyl group and the hydroxy groups of this compound lying adjacent thereto. In turn, from the number of deprotonated groups, the corresponding number of counter-cations is obtained (depending on their charge). Thus for example for a compound of the formula (X) with one carboxyl and one hydroxy group on which such as salt is based, it is found that with complete deprotonation of the groups a doubly negatively charged anion is present, from which in turn the number of positive charges is found (here: two), which must be provided by the counter-cation(s). Particularly preferably, these counter-cations are cations selected from the group consisting of $Na^+$, $K^+$, $NH_4^+$, $Ca^{2+}$, $Mg^{2+}$, $Al^{3+}$ and $Zn^{2+}$.

Particularly preferable therefore is a salt of a compound of the formula (X) or a mixture (as respectively described above) containing or consisting of one, two or more different salts of compounds of the formula (X), preferably of compounds of the formula (X) previously designated as preferable, and optionally one, two or more different salts of compounds of the formula (Y), preferably of compounds of the formula (Y) previously designated as preferable, or one or more different compounds of the formula (X) and/or one or more different salts of compounds of the formula (X), and optionally one or more different compounds of the formula (Y) and/or one or more different salts of compounds of the formula (Y), wherein the counter-cation(s) of one, several or all of the salts of compounds of the formula (X) and/or compounds of the formula (Y) is or are selected from the group consisting of $Na^+$, $K^+$, $NH_4^+$, $Ca^{2+}$, $Mg^{2+}$, $Al^{3+}$ and $Zn^{2+}$.

As aforesaid, one, several or all of the compounds of the formula (X) or salts of compounds of the formula (X) to be used according to the invention, and optionally one, several or all of the compounds of the formula (Y) or salts of compounds of the formula (Y) can also be used in the form of plant extracts, in particular in the form of extracts from *Eriodictyon* ssp., in particular from *Eriodictyon californicum* and/or *Eriodictyon angustifolium*, optionally after treatment with a base for conversion of the compound(s) of the formula (X) or (Y) into a salt.

Preferably the dried plant parts (see above) used in the context of the present invention e.g. fresh or dried roots, root bark, tubers, onions, other under- or aboveground storage organs, accessory fruit, fruit, seeds, bark, wood, pulp, bast, stems, stalks, leaves or flower [parts], preferably the stems, stalks, leaves and flower [parts], preferably in comminuted form, are extracted with a solvent suitable for food and luxury consumables at temperatures in the range between the freezing point and the boiling point of the particular solvent or solvent mixture, then filtered and the filtrate wholly or partially concentrated, preferably by distillation, or freeze- or spray-drying. The crude product thus obtained can then be still further worked up, for example back-extracted, purified via distribution, absorption, exclusion, affinity or ion chromatography, distilled, sublimed, purified with adsorbents such as activated charcoal, bentonite, diatomaceous earth, etc., treated enzymatically (e.g. with glycosidases to increase yield of non-sugar-containing molecules), with acid (e.g. under pressure), with suitable basic solutions e.g. of hydroxides, carbonates or hydrogen carbonates of sodium, potassium, calcium, magnesium and zinc, with acidic ion exchangers or with steam, as a rule at pressures from 0.01 mbar to 100 bar, preferably at 1 mbar to 20 bar, treated with an auxiliary and carrier substance and optionally dried (e.g. spray dried) and/or taken up in a solvent suitable for food and luxury consumables and/or for cosmetic and dermatological uses.

Suitable solvents for the extraction are in particular water, ethanol, methanol, propylene glycol, glycerine, acetone, dichloromethane, ethyl acetate, diethyl ether, hexane, heptane, triacetin, plant oils or fats, supercritical carbon dioxide and mixtures thereof.

Preferable auxiliary or carrier substances are maltodextrin, starch, natural or synthetic polysaccharides and/or plant gums such as modified starches or gum Arabic, colouring agents, e.g. permitted food dyes, colouring plant extracts, stabilizers, preservatives, antioxidants and viscosity-modifying substances.

Particularly preferable is a mixture according to the invention (as described above), wherein the mixture comprises a plant extract or consists thereof, preferably an extract from *Eriodictyon* ssp., particularly preferably an extract from *Eriodictyon californicum* and/or *Eriodictyon angustifolium*. A mixture preferred according to the invention or a mixture preferably to be used according to the invention (as described above) according to one embodiment of the present invention particularly preferably comprises or consists of (1.) an extract from *Eriodictyon californicum*, (2.) an extract from *Eriodictyon angustifolium* or (3.) an extract from *Eriodictyon californicum* and *Eriodictyon angustifolium*, i.e. an extract from plants or plant parts from both *Eriodictyon californicum* and also *Eriodictyon angustifolium*, or (4.) a mixture of an extract from *Eriodictyon californicum* and an extract from *Eriodictyon angustifolium*.

Particularly preferably, a mixture according to the invention or a mixture preferably to be used according to the invention (as respectively described above) consists of an extract from *Eriodictyon* ssp., particularly preferably of an extract from *Eriodictyon californicum* and/or *Eriodictyon angustifolium*. The production of a plant extract from *Eriodictyon californicum* and/or *Eriodictyon angustifolium* is described later herein.

As described above, one aspect of the present invention relates in particular to a preparation used for food or enjoyment, in particular a food, luxury consumable or drink, or a cosmetic or dermatological preparation, in particular a preparation suitable for the treatment, protection and/or care of the skin, nails and/or hair and of the oral cavity (in particular of the gingiva and the teeth), or a pharmaceutical preparation, for the treatment of inflammatory states of the body of warm-blooded animals. As regards the composition of such a preparation, reference is essentially made to the above explanations.

According to a preferable embodiment of the present invention, the proportion of the total quantity of compounds of the formula (X) and (optionally) compounds of the formula (Y) and salts thereof in the preparation lies in the range from 0.0001 to 30 wt. %, preferably in the range from 0.001 to 20 wt. %, particularly preferably in the range from 0.001 to 5 wt. %, based on the total weight of the preparation.

Preparations according to the invention, in particular preparations according to the invention used for food or enjoyment, in the context of the present invention can in particular be embodied as compositions suitable for consumption (as described below). The preparations used for food or enjoyment in the sense of the present invention can also be used as semifinished goods for the production of further preparations used for food or enjoyment.

The preparations according to the invention used for food or enjoyment and corresponding semifinished goods and preparations or compositions suitable for consumption are as a rule products which are intended to be introduced into the human oral cavity, to remain there for a certain time and then either be consumed (e.g. ready-to-eat foods, see below) or removed again from the oral cavity (e.g. chewing gums). Thus these products include all articles or substances which are intended to be ingested by people, in the processed, partially processed or unprocessed state. In particular, compositions suitable for consumption are articles which products which are added to foods during the production, processing or modification thereof and are intended to be introduced into the human oral cavity, in particular with the said food. Accordingly, such compositions can in turn be contained in (further) ready-to-use or ready-to-eat preparations used for food or enjoyment (in the context of the present text, ready-to-use or ready-to-eat preparations used for food or enjoyment are in particular foods, especially ready-to-eat foods (see below)). In addition, such compositions can be a component of a semifinished product which optionally can in turn be used for the production of ready-to-use or ready-to-eat preparations used for food or enjoyment.

Preparations used for food or enjoyment in the sense of the present invention are in particular ready-to-use or ready-to-eat preparations, in particular foods, especially ready-to-eat foods, e.g. bakery products (e.g. bread, dry biscuits, cakes, other pastries), confectionery (e.g. chocolates, chocolate bar products, other products in bars, fruit gum, hard and soft caramels, chewing gum), alcoholic or non-alcoholic drinks (e.g. coffee, tea, wine, wine-containing drinks, beer, beer-containing drinks, liqueurs, spirits, brandies, fruit-containing soft drinks, isotonic drinks, refreshment drinks, nectars, fruit and vegetable juices, fruit or vegetable juice preparations), instant drinks (e.g. instant cocoa drinks, instant tea drinks, instant coffee drinks), meat products (e.g. ham, fresh sausage or raw sausage preparations, spiced or marinated fresh or pickled meat products), eggs or egg products (dried egg, egg white, egg yolk), cereal products (e.g. breakfast cereals, muesli bars, prefermented prepared rice products), dairy products (e.g. milk drinks, milk-based ice cream, yoghurt, kefir, cream cheese, soft cheese, hard cheese, dried milk powder, whey, butter, buttermilk, partially or fully hydrolyzed milk protein-containing products), products from soya protein or other soya bean fractions (e.g. soya milk and products prepared therefrom, soya lecithin-containing preparations, fermented products such as tofu or tempe or products prepared therefrom, soya sauces), fruit preparations (e.g. preserves, fruit-flavoured ice cream, fruit sauces, fruit fillings), vegetable preparations (e.g. ketchup, sauces, dried vegetables, deep-frozen vegetables, prefermented vegetables, vegetables marinated in vinegar, preserved vegetables), nibbles (e.g. baked or fried potato crisps or potato dough products, bread dough products, maize- or peanut-based extruded products), fat and oil-based products or emulsions thereof (e.g. mayonnaise, remoulade, dressings, spice preparations), other ready-to-serve meals and soups (e.g. dried soups, instant soups, prefermented soups), spices, spice mixtures and in particular seasonings), which are for example used in the snacks field.

Preferable carrier substances contained in such (preferably spray dried) compositions according to the invention are silicon dioxide (silicic acid, silica gel), carbohydrates and/or carbohydrate polymers (polysaccharides), cyclodextrins, starches, degraded starches (starch hydrolyzates), chemically or physically modified starches, modified celluloses, gum Arabic, ghatti gum, tragacanth, karaya, carrageenan, guar gum, carob flour, alginates, pectin, inulin or xanthan gum.

Preferable starch hydrolysates are maltodextrins and dextrins, where here again maltodextrins with DE values in the range 5 to 20 are particularly preferable. Here it is unimportant what plant originally provided the starch for the production of the starch hydrolyzates. Maize-based starches and starches from tapioca, rice, wheat or potatoes in particular are suitable and readily available. Here previously described carrier substances (e.g. silicon dioxide) can advantageously function as free-flow agents.

The preparations according to the invention, which as well as one or more compounds of the formula (X) and/or salts thereof or a suitable mixture also contain one or more solid carrier substances can for example be produced by mechanical mixing processes, wherein at the same time a comminution of the particles can take place, or by means of spray-drying. As described above, compositions according to the invention which contain solid carrier substances and are produced by means of spray-drying are preferable; concerning the spray-drying, reference is made to U.S. Pat. No. 3,159,585, U.S. Pat. No. 3,971,852, U.S. Pat. No. 4,532,145 or U.S. Pat. No. 5,124,162.

Preferable preparations containing carrier substances (as described above) which have been produced by means of spray-drying preferably have a mean particle size in the range from 30 to 300 μm and preferably a residual moisture content of 5 wt. % or less.

According to one embodiment of the present invention, the weight ratio of the total mass of compounds of the formula (X) and optionally of the formula (Y) and salts thereof in a preparation described herein containing one or more (suitable for consumption, solid) carrier substances (as described above) to the total mass of (suitable for consumption, solid) carrier substances preferably lies in the range from 1:10 to 1:100000, preferably in the range from 1:50 (preferably from 1:100) to 1:20000, particularly preferably in the range from 1:100 (preferably from 1:1000) to 1:5000, based on the dry mass of the preparation.

In a preparation (as described above) containing one or more (suitable for consumption, solid) carrier substances (as described above), the proportion of the total quantity of compounds of the formula (X) and optionally of the formula (Y), salts thereof and (suitable for consumption, solid) carrier substances, based on the total weight of the preparation, preferably lies in the range from 70 to 100 wt. %, preferably in the range from 85 to 100 wt. %.

The preparations according to the invention used for food or enjoyment, as well as normally used animal or plant raw materials, can additionally contain water, squalane or squalene, natural oils (e.g. olive oil, sunflower oil, soya oil, peanut oil, rape oil, almond oil, palm oil, coconut oil, palm nut oil, borage seed oil and more of the like), natural ester oils (e.g. jojoba oil), fats, waxes and other natural fatty substances, carbohydrates, for example glucose, sucrose or lactose, sweeteners, for example aspartame, cyclamate, saccharin, xylitol or sorbitol, bitter substances, for example caffeine or quinine, bitterness-suppressing substances, for example lactisol, flavour-intensifying substances, for example sodium glutamate or inositol phosphate, amino acids, for example glycine, alanine, leucine, isoleucine, valine, proline, lysine, asparagine, aspartic acid, glutamine, glutamic acid, tryptophan, phenylalanine, tyrosine, threonine, serine, cystine, cysteine, methionine, hydroxyproline, arginine or histidine, peptides, proteins, enzymes, fruit acids, preferably lactic acid, malic acid or citric acid, as well as emulsifiers, which can advantageously be selected from the group of the ionic, nonionic, polymeric, phosphate-containing and zwitterionic emulsifiers, and in particular one or more thickeners, which can advantageously be selected from the group of the polysaccharides or derivatives thereof, e.g. hyaluronic acid, guar gum, carob flour, xanthan gum or allulose derivatives, and natural, nature-identical or synthetic aromas and salts, for example sodium chloride or potassium chloride.

The cosmetic and dermatological preparations according to the invention can contain cosmetic auxiliary agents and/or additives such as are normally used in such preparations, e.g. sunscreens (e.g. organic or inorganic light filter substances, preferably micropigments), preservatives, bactericides, fungicides, virucides, cooling active substances, plant extracts, inflammation-inhibiting active substances, wound healing accelerating substances (e.g. chitin or chitosan and derivatives thereof), film-forming substances (e.g. polyvinylpyrrolidones or chitosan or derivatives thereof), common antioxidants, vitamins (e.g. vitamin C and derivatives, tocopherols and derivatives, vitamin A and derivatives), 2-hydroxycarboxylic acids (e.g. citric acid, malic acid, L-, D-, or dl-lactic acid), skin lighteners (e.g. kojic acid, hydroquinone or arbutin), skin colorants (e.g. walnut extracts or dihydroxyacetone), perfumes, substances for prevention of foaming, colorants, pigments which have a colorant action, thickeners, surfactant substances, emulsifiers, plasticizing, moistening and/or humectant substances (e.g. glycerine or urea), fats, oils, unsaturated fatty acids or derivatives thereof (e.g. linolic acid, alpha-linolenic acid, gamma-linolenic acid or arachidonic acid and their respective natural or synthetic esters), waxes or other normal components of a cosmetic or dermatological formulation such as alcohols, polyols, polymers, foam stabilizers, electrolytes, organic solvents, silicone derivatives or chelating agents (e.g. ethylendiaminetetraacetic acid and derivatives).

The particular quantities to be used can easily be determined by those skilled in the art by simple testing, depending on the nature of the particular product.

Preferably preparations according to the invention (as described above) additionally contain one or more antioxidants, where the antioxidant or antioxidants is/are not a compound or compounds of the formula (X) or a salt thereof. In particular, as such antioxidants, all antioxidants suitable or usual for the respective use can be used. The antioxidant or antioxidants is or are preferably selected from the group consisting of amino acids (e.g. glycine, histidine, 3,4-dihydroxyphenylalanine, tyrosine, tryptophan) and derivatives thereof, imidazoles (e.g. urocanic acid) and derivatives thereof, peptides (D,L-carnosine, D-carnosine, L-carnosine, anserine) and derivatives thereof, carotenoids, carotenes (e.g. beta-carotene, alpha-carotene, lycopene) and derivatives thereof, chlorogenic acid and derivatives thereof, lipoic acid and derivatives thereof, aurothioglucose, propylthiouracil and other thiols (e.g. thioredoxin, glutathione, cysteine, cystine, cystamine and glycosyl and N-acyl derivatives thereof or alkyl esters thereof) and salts thereof, dilauryl thiodipropionate, distearyl thiodipropionate, thiodipropionic acid and derivatives thereof and phenolic acid amides of phenolic benzylamines (e.g. homovanillic acid, 3,4-dihydroxyphenylacetic acid, ferulic acid, sinapinic acid, caffeic acid, dihydroferulic acid, dihydrocaffeic acid, vanillomandelic acid- or 3,4-dihydroxymandelic acid amides of 3,4-dihydroxybenzyl, 2,3,4-trihydroxybenzyl- or 3,4,5-trihydroxybenzyl-amine), catechol oximes or catechol oxime ethers (e.g. 3,4-dihydroxybenzaldoxime or 3,4-dihydroxybenzaldehyde O-ethyloxime), also (metal) chelators (e.g. 2-hydroxyfatty acids, phytic acid, lactoferrin), humic acid, bile acids, bile extracts, bilirubin, biliverdin, folic acid and derivatives thereof, ubiquinone and ubiquinol and derivatives thereof, vitamin C and derivatives thereof (e.g. ascorbyl palmitate, magnesium ascorbyl phosphate, ascorbyl acetate), tocopherols and derivatives (e.g. alpha-tocopherol, vitamin E acetate), vitamin A and derivatives (e.g. vitamin A palmitate), rutinic acid and derivatives thereof, flavonoids (e.g. quercetin, alpha-glucosylrutin) and derivatives thereof, phenolic acids (e.g. gallic acid, ferulic acid) and derivatives thereof (e.g. gallic acid propyl ester, ethyl ester and octyl ester), furfurylideneglucitol, dibutylhydroxytoluene, butylhydroxyanisole, uric acid and derivatives thereof, mannose and derivatives thereof, zinc and derivatives thereof (e.g. ZnO, $ZnSO_4$), selenium and derivatives thereof (e.g. selenomethionine), stilbene and derivatives thereof (e.g. stilbene oxide, resveratrol) and the derivatives of these named (active) substances suitable in the context of the present invention.

Furthermore, a preparation according to the invention (as described above), in particular a cosmetic or dermatological preparation according to the invention, can include one or more UV-A and/or UV-B filter substances. The filter substance or substances here are preferably selected from the group consisting of 3-benzylidenecamphor derivatives (e.g. 3-(4-methylbenzylidene)-dl-camphor), aminobenzoic acid derivatives (e.g. 4-(N,N-dimethylamino)benzoic acid 2-ethylhexyl ester or menthyl anthranilate), 4-methoxy-cinnamates (e.g. 2-ethylhexyl p-methoxycinnamate or isoamyl p-methoxycinnamate), benzophenones (e.g. 2-hydroxy-4-methoxybenzophenone), singly or multiply sulphonated UV filters [e.g. 2-phenylbenzimidazol-5-sulphonic acid, sulisobenzone or 1,4-bis(benzimidazolyl)-benzene-4,4',6,6'-tetrasulphonic acid or 3,3'-(1,4-phenylene-dimethylidene)-bis(7,7-dimethyl-2-oxo-bicyclo[2,2,1]heptane-1-methane-sulphonic acid) and salts thereof], salicylates (e.g. 2-ethylhexyl salicylate or homomethyl salicylate), triazines {e.g. 2,4-bis-[4-(2-ethylhexyloxy)-2-hydroxyphenyl]-6-(4-methoxyphenyl)-1,3,5-triazine, 4,4'-([6-([(1,1-dimethyl-ethyl)-aminocarbonyl]phenylamino)-1,3,5-triazin-2,4-diyl]-diimino)bisbenzoic acid bis-(2-ethylhexyl)ester)}, 2-cyanopropenoic acid derivatives (e.g. 2-ethylhexyl 2-cyano-3,3-diphenyl-2-propenoate, dibenzoyl derivatives (e.g. 4-tert-butyl-4'-methoxydibenzoylmethane), polymer-bound UV filters (e.g. polymers of N-[2-(or 4)-(2-oxo-3-bornylidene)methyl]benzylacrylamide) or pigments (e.g. titanium dioxides, zirconium dioxides, iron oxides, silicon dioxides, manganese oxides, aluminium oxides, cerium oxides or zinc oxides). Such a preparation according to the invention is preferably a sunscreen for skin and/or hair.

Accordingly, the present invention particularly preferably relates to a preparation according to the invention (as described above) additionally comprising (II) one or more antioxidants, wherein the antioxidant or antioxidants is or are not a compound(s) of the formula (x) or a salt thereof and is or are preferably selected from the group consisting of beta-carotene, lycopene, chlorogenic acid, 2-hydroxy fatty acids, bilirubin, folic acid, ubiquinone, ubiquinol, vitamin C and derivatives thereof, in particular ascorbyl palmitate, magnesium ascorbyl phosphate and ascorbyl acetate; tocopherols and derivatives thereof, in particular alpha-tocopherol and vitamin E acetate; vitamin A and derivatives thereof, in particular vitamin A palmitate; rutinic acid, quercetin, ferulic acid, dibutylhydroxytoluene, butylhydroxyanisole and uric acid,
and/or
(III) one or more UV-A and/or UV-B filter substances, where one, several or all of the UV-A and/or UV-B filter substances is or are preferably selected from the group consisting of 3-(4-methylbenzylidene)-dl-camphor, menthyl anthranilate, 2-ethylhexyl p-methoxycinnamate, isoamyl p-methoxycinnamate, 2-hydroxy-4-methoxy-benzophenone, 2-phenylbenzimidazol-5-sulphonic acid and salts thereof, 1,4-bis(benzimidazolyl)-benzene-4,4',6,6'-tetrasulphonic acid and salts thereof, 2-ethylhexyl salicylate, homomethyl salicylate, 2,4-bis-[4-(2-ethylhexyloxy)-2-hydroxyphenyl]-6-(4-methoxyphenyl)-1,3,5-triazine, 4,4'-([6-([(1,1-dimethylethyl)-amino-carbonyl]phenylamino)-1,3,5-triazin-2,4-diyl]diimino)bisbenzoic acid bis-(2-ethylhexyl)ester), 2-ethylhexyl 2-cyano-3,3-diphenyl-2-propenoate, 4-tert-butyl-4'-methoxydibenzoylmethane, titanium dioxide, silicon dioxide and zinc oxide.

Particularly preferable is such a preparation according to the invention, wherein
the proportion of the total quantity of component (II) in the preparation, based on the total weight of the preparation, is 0.0001 to 30 wt. %, preferably 0.001 to 20 wt. %, particularly preferably 0.001 to 5 wt. %,
and/or
the proportion of the total quantity of component (III) in the preparation, based on the total weight of the preparation, is 0.1 to 30 wt. %, preferably 0.5 to 10 wt. %.

The (pharmaceutical) preparations in the sense of the present invention used for the treatment of inflammatory states of warm-blooded animals can also be used as semifinished goods for the production of further pharmaceutical preparations used for the treatment of inflammatory states of warm-blooded animals.

The pharmaceutical preparations according to the invention used for the treatment of inflammatory states of warm-blooded animals, and corresponding semifinished goods are as a rule products which are intended to be introduced into the body of warm-blooded animals or used on the body of warm-blooded animals.

The pharmaceutical preparations according to the invention used for the treatment of inflammatory states of warm-blooded animals in the sense of the present invention are preferably ready-to-use preparations, in particular medicaments and medicinal products, preferably in the following forms: solid galenical forms (such as for example tablets (with and without coating, with and without modified release), sugar-coated tablets (with and without coating, with and without modified release), capsules (soft or hard gelatine capsules with and without modified release) granules (with and without modified release), powders (with and without modified release), suppositories (with and without coating, with and without modified release) lozenges and chewing gums), and liquid forms (such as for example solutions, suspensions, emulsions, syrups (colloquially cough syrup), mouthwashes, gargle solutions, throat sprays or nasal sprays, nasal drops, nasal rinse solutions, nasal powders, nasal ointments or ear drops, ear sprays, ear rinse solutions, ear powders and aural tampons), and semisolid forms (such as for example hydrophobic ointments including for example: hydrocarbon gels, lipogels, silicone gels, oleogels and water-absorbing ointments including for example absorption bases, hydrophilic ointments, hydrophilic gels (hydrogels) or pastes, and inhalants (such as for example compressed gas dispenser inhalers, powder inhalers, inhalers with atomisers, and inhalation concentrates for the preparation of inhalations), and active substance-containing plasters or other therapeutic systems.

The pharmaceutical preparations according to the invention can contain (further) pharmaceutical auxiliary and/or additive substances, such as are normally used in such preparations, e.g. active substances from the group of the non-steroidal anti-inflammatories, antibiotics, systemically active steroids, anti-TNF-alpha antibodies or other biotechnologically produced active substances and/or pure substances such as budesonide, sulfasalazine, azathioprine/6-mercaptopurine or methotrexate. And for example fillers (e.g. cellulose, calcium carbonate), free-flow and anticaking agents (e.g. talc, magnesium stearate), coatings (e.g. polyvinyl acetate phthalate, hydroxypropyl-methylcellulose phthalate), disintegrants (e.g. starch, crosslinked polyvinylpyrrolidone), plasticizers (e.g. triethyl citrate, dibutyl phthalate) substances for granulation (lactose, gelatine), retardation (e.g. poly(meth)acrylic acid methyl/ethyl/2-trimethylaminoethyl ester copolymers in dispersion, vinyl acetate/crotonic acid copolymers) and compacting (e.g. microcrystalline cellulose, lactose), solvent, suspension or dispersion agents (e.g. water, ethanol), emulsifiers (e.g. cetyl alcohol, lecithin), substances for modification of the rheological properties (silicon dioxide, sodium alginate), substances for microbial stabilization (e.g. benzalkonium chloride, potassium sorbate), preservatives and antioxidants (e.g. DL-alpha-tocopherol, ascorbic acid), substances for modification of the pH (lactic acid, citric acid), propellant or inert gases (e.g. fluorinated chlorohydrocarbons, carbon dioxide), colorants (iron oxides, titanium dioxide), ointment bases (e.g. paraffins, beeswax), inter alia as described in the technical literature (e.g. Schmidt, Christin. Active and Auxiliary Substances for Individual and Bulk Formulation, and Large-scale Manufacture. 1999; Wissenschaftliche Verlagsgesellschaft mbH Stuttgart or Bauer, Frömming Führer. Textbook of Pharmaceutical Technology. $8^{th}$ Edition, 2006. Wissenschaftliche Verlagsgesellschaft mbH Stuttgart).

The particular quantities to be used can easily be determined by those skilled in the art by simple testing, depending on the nature of the particular product.

According to one aspect of the present invention, a preparation according to the invention wherein the proportion of the total quantity of compounds of the formula (X) and optionally of the formula (Y) and salts thereof in the preparation lies in the range from 0.0001 to 30 wt. %, preferably in the range from 0.001 to 20 wt. %, and particularly preferably in the range from 0.001 to 5 wt. %, based on the total weight of the preparation, is preferable.

(Further) preferable methods for the production of a preferable mixture or preparation according to the invention (as described above) are described below.

Such a method preferably comprises the steps (a) extraction of plant material (as described above), preferably as described above as preferable, and (b) concentration of extracted compounds of the formula (X) and optionally additionally of the formula (Y) and/or salts thereof (as described above) by partial or complete removal of other extracted compounds and optionally removal of extractants and/or solvents, preferably so that the proportion of the total quantity of compounds of the formula (X) and optionally (Y) and salts thereof in the mixture obtained, based on the total weight of the mixture, is 0.0001, preferably 15 to 100 wt. %, preferably 25 to 90 wt. % (preferably 100 wt. %), and particularly preferably 45 to 85 wt. % (preferably 100 wt. %).

For example, a mixture or preparation according to the invention (as described above) can also be produced by a method according to the invention (as described above), wherein the method is carried out following the method described in the publication in WO2004041804 (for the obtention of a crude extract from *Eriodictyon californicum* and/or *Eriodictyon angustifolium*).

The steps of such a method according to the invention (partly based on the method according to WO2004041804) are briefly summarized below:

a) Plant material from *Eriodictyon californicum* and/or *Eriodictyon angustifolium* is singly or multiply extracted with a non-water-miscible extractant (optionally with heating up to the relevant boiling point).

b) The crude extract thus obtained (containing compounds of the formula X and/or of the formula Y to be used according to the invention and other extracted compounds such as for example rosmarinic acid) is separated from the plant material.

c) The crude extract (containing compounds of the formula X and/or of the formula Y to be used according to the invention and other extracted compounds such as for example rosmarinic acid) is preferably concentrated and interim stocked.

d) Precipitated solids (waxes) are optionally removed.

e) The (optionally dewaxed) crude extract (containing compounds of the formula (X) and optionally of the formula (Y) to be used according to the invention and other extracted compounds such as for example rosmarinic acid) is optionally treated with activated charcoal and separated from the solid.

Through the following further steps, the compounds of the formula (X) and optionally of the formula (Y) to be used according to the invention can be further concentrated in the organic phase:

f) (Preferably complete) removal of the organic solvent of the organic phase by evaporative or permeative methods.

g) Taking up of the residue (comprising compounds of the formula (X) and optionally of the formula (Y) to be used according to the invention) in methanol.

h) Removal of the methanol-insoluble components of the mixture (comprising compounds of the formula (X) and optionally of the formula (Y) to be used according to the invention and other extracted compounds) by filtration.

In the mixture present according to this method after step e), the proportion of the total quantity of compounds of the formula (X) and optionally of the formula (Y) and salts thereof, based on the dry mass of the mixture (j), according to a preferable embodiment of the present invention lies in the range from 1 to 35 wt. %, preferably in the range from 20 to 35 wt. %.

In the mixture (h) present according to this method according to the invention after step h), the proportion of the total quantity of compounds of the formula (X) and optionally of the formula (Y) and salts thereof, based on the dry mass of the mixture (h), preferably lies in the range from 40 to 100 wt. %, preferably in the range from 45 to 85 wt. %.

The mixtures (e) and (h) and the mixtures present after the steps f) and g), in particular mixture (h), can each be mixtures according to the invention (as described above).

Evaporative or pervaporative methods can for example be distillation, sublimation, steam distillation, freeze drying, pervaporative membrane methods or spray-drying, and particular appropriate auxiliary and/or carrier substances can be added thereto.

According to an alternative embodiment of a method according to the invention for the production of a mixture as described above, a methanolic crude extract is obtained from *Eriodictyon* ssp., preferably *Eriodictyon californicum* and/or *Eriodictyon angustifolium*, which contains extracted compounds of the formula (X) and optionally of the formula (Y) and other extracted compounds (in particular rosmarinic acid). Herein also, the extracted compounds of the formula (X) and optionally of the formula (Y) and/or salts of these extracted compounds in the mixture are concentrated by partial or complete removal of other extracted compounds and optionally removal of extractants and/or solvents (each time preferably analogously to the previously described method design), so that the proportion of the total quantity of compounds of the formula (X) and optionally of the formula (Y) and salts thereof in the mixture, based on the dry mass of the mixture, for example preferably lies in the range from 40 to 100 wt. %, particularly preferably 45 to 85 wt. %.

Such concentration is preferably attained by FCPC (Fast Centrifugal Partition Chromatography, Guido F. Pauli, Samuel M. Pro, J. Brent Friesen Countercurrent Separation of Natural Products *J. Nat. Prod.* 2008, 71, 1489-1508) and/or HTLC (High Temperature Liquid Chromatography; WO2006111476) and/or preparative HPLC (High Pressure Liquid Chromatography).

According to a preferable embodiment of the present invention, the extracts or mixtures described herein are incorporated in the form of emulsions into liposomes, for example starting from phosphatidylcholine, into microspheres, into nanospheres or also into capsules, granules or extrudates, for example of starch, starch derivates, cellulose or cellulose derivates (for example hydroxypropylcellulose), other polysaccharides (for example alginates), natural fats, natural waxes (for example beeswax, carnauba wax) or of proteins, for example gelatine.

In connection with the present invention, a prophylactic and/or therapeutic method as described above, with the following step, is also described:

Contacting of (human or animal) tissue and/or of the (human or animal) cells with an inflammation-inhibiting effective quantity of a compound of the formula (X), a salt of a compound of the formula (X), an above-described mixture, in particular of a mixture which additionally comprises a compound of the formula (Y) and/or a salt thereof, as respectively described above, or of a preparation as described above.

The contacting of the tissue or the cells with one or more compounds of the formula (X) and optionally additionally one or more compounds of the formula (Y) and/or salts thereof or a mixture or preparation according to the invention (as respectively described above) here—depending on the tissue to be treated or the cells to be treated—can also be effected by external (e.g. topical) or internal use (e.g. oral application).

The following examples serve to clarify the invention, without thereby restricting this.

EXAMPLES

Example 1

Production of a Methanolic Extract from *Eriodictyon angustifolium*

Boiling water was poured over 500 g of dried leaves of *Eriodictyon angustifolium* and stirred for one hour in order to swell the plant material and prepare it for the further extraction. The plant material was filtered off, dried and extracted twice with 2.0 l methanol each time at room temperature for one hour with stirring. The methanolic extract was filtered off, dried under vacuum and stored overnight in the high vacuum drying oven to remove residual solvent. The extraction yielded 84.53 g of dark green extract.

Example 2

Isolation of the Individual Compounds from *Eriodictyon angustifolium* by Means of FCPC The methanolic extract of *E. angustifolium* according to Example 1 was separated and fractionated by means of FCPC using a two-phase solvent system (heptane/ethyl acetate/methanol/water 5:4:4:5). As well as flavones described in the literature, four compounds of the formula (X) could be isolated. Structure elucidation was effected by means of one- and two-dimensional NMR experiments.

| Compound | Molecular weight [g/mol] | Retention time [mins] |
|---|---|---|
| Erionic acid F (6) | 358 | 17.0-19.0 (ascending) |
| Erionic acid C (3) | 374 | 64.0-69.0 (ascending) |
| Erionic acid A (1) | 390 | 52.0-54.0 (descending) |
| Erionic acid B (2) | 390 | 55.0-56.0 (descending) |

FCPC Conditions:
FCPC: bench scale FCPC model, version A (Kromaton Technologies, Angers, France)
Rotor: 200 ml (semi-preparative)
Injector: Kronlab High Speed Valve (Kronlab Chromatography Technology, Dinslaken)
Injection loop: 10 ml
Pumps: Knauer HPLC pump 64 (Knauer Berlin)
Pulse damper: Type 55073 (BESTA-Technik, Wilhelmsfeld)
Detector: ELSD SEDEX 75 Light scattering detector (S.E.D.E.R.E, Alfortville, Cedex, France)
Fraction collector: Labocol Vario 2000 (Labomatic, Weil am Rhein)
Software: PrepCon (SCPA GmbH, Weye-Leeste); Version 5.03.009, SCPA GmbH 2003
Solvent system: upper phase: heptane/ethyl acetate (5/4) lower phase: methanol/water (4/5)
Ascending mode: methanol/water as stationary phase
Descending mode: heptane/ethyl acetate as stationary phase
Stock solution: 60 mg/10 ml stationary/mobile Phase (1:1)
Flow rate: 8 ml/min (ascending mode)
   10 ml/min (descending mode)
Fractionation: 40 fractions of 8 ml (ascending mode)
   30 fractions of 10 ml (descending mode)
Analytical Data:

| Pos. | $\delta_c$, mult. | $\delta_H$ (J in Hz) | $\delta_c$, mult. | $\delta_H$ (J in Hz) |
|---|---|---|---|---|
| | Erionic acid F (6) (400 MHz, CH3OD) | | Erionic acid C (3) (400 MHz, CH3OD) | |
| 1 | 123.2 | | n.d. | |
| 2 | 130.8 | 7.63, d (2.1) | 131.1$^a$ | 6.92, s |
| 3 | 129.4 | | 130.3 | |
| 4 | 158.4 | | 158.4 | |
| 5 | 129.4 | | 125.6 | |
| 6 | 130.5 | 7.71, d (2.1) | 130.8$^a$ | 6.92, s |
| 7 | 170.8 | | 171.1 | |
| 8 | 29.0 | 2.61, m | 29.2 | 2.59, m |
| 9 | 33.8 | 1.95, m | 33.9 | 1.95, m |
| | | 1.61, m | | 1.61, m |
| 10 | 46.2 | 2.65, m | 46.5 | 2.66, m |
| 11 | 216.1 | | 217.4 | |
| 12 | 44.5 | 3.18, m | 42.2 | 3.19, m |
| 13 | 117.2 | 5.23, dd (7.1, 7.1) | 117.5 | 5.24, m |
| 14 | 136.7 | | 136.8 | |
| 15 | 25.9 | 1.77, s$^a$ | 25.9 | 1.72, s |
| 16 | 16.9 | 1.12, d (7.0) | 16.9 | 1.12, d (7.0) |
| 17 | 17.9a | 1.72, s$^a$ | 18.3 | 1.61, s |
| 18 | 29.4 | 3.33, d (7.3) | 29.2 | 3.40, d (7.4) |
| 19 | 123.0 | 5.32, dd (7.3, 7.3) | 124.2 | 5.61, dd (7.4, 7.4) |
| 20 | 134.2 | | 137.8 | |
| 21 | 26.0 | 1.72, s$^b$ | 69.1 | 3.99, s |
| 22 | 18.1a | 1.60, s$^b$ | 13.9 | 1.76, s |
| | Erionic acid A (1) (400 MHz, DMSO) | | Erionic acid B (2) (600 MHz, CH$_3$OD) | |
| 1 | 127.7$^a$ | | 130.3$^a$ | |
| 2 | 128.7$^b$ | 7.52, s | 130.4$^a$ | 7.57, d (2.1) |
| 3 | 128.3$^a$ | | 129.6$^a$ | |
| 4 | 156.5 | | 155.0$^b$ | |
| 5 | 121.0 | | 131.4$^a$ | |
| 6 | 128.9$^b$ | 7.52, s | 130.4$^a$ | 7.56, d (2.1) |
| 7 | 169.1 | | 170.2 | |
| 8 | 27.4 | 2.55, m | 28.9 | 2.58, m |
| 9 | 32.6 | 1.83, m | 34.6 | 1.96, m |
| | | 1.51, m | | 1.61, m |
| 10 | 42.7 | 2.85, ddq (6.8, 6.8, 6.8) | 44.4 | 2.86, ddq (6.8, 6.8, 6.9) |
| 11 | 203.4 | | 207.0 | |
| 12 | 123.8 | 6.27, d (15.8) | 125.6 | 6.29, d (15.8) |
| 13 | 154.3 | 6.83, d (15.8) | 154.9$^b$ | 6.83, d (15.8) |
| 14 | 69.1 | | 71.2 | |
| 15 | 29.0 | 1.22, s$^a$ | 29.3 | 1.30, s$^a$ |

-continued

| Pos. | $\delta_c$, mult. | $\delta_H$ (J in Hz) | $\delta_c$, mult. | $\delta_H$ (J in Hz) |
|---|---|---|---|---|
| 16 | 16.2 | 1.07, d (6.9) | 16.8 | 1.13, d (6.9) |
| 17 | 29.0 | 1.23, s$^a$ | 29.3 | 1.29, s$^a$ |
| 18 | 27.6 | 3.33, d (7.3) | 32.4 | 3.02, dd (5.4, 16.5) |
|    |      |               |      | 2.74, dd (7.8, 16.5) |
| 19 | 120.8 | 5.50, dd (7.3, 7.3) | 70.5 | 3.75, dd (7.8, 5.4) |
| 20 | 136.2 |               | 78.4 |      |
| 21 | 66.1 | 3.83, s | 24.3$^c$ | 1.36, s$^a$ |
| 22 | 13.1 | 1.65, s | 21.0$^c$ | 1.25, s$^a$ |

$^{a,b}$interchangeable signals

Example 3

Isolation of the Individual Compounds from *Eriodictyon angustifolium* by Means of High Temperature Liquid Chromatography (HTLC)

The methanolic extract of *E. angustifolium* according to Example 1 was separated and fractionated by means of HTLC using a polymer-based semi-preparative column with water-ethanol gradients under isothermal conditions (120° C.). In addition to flavones described in the literature, four substances could be isolated.

| Compound | Molecular weight [g/mol] | Retention time [mins] |
|---|---|---|
| Erionic acid C (3) | 374 | 14.5-15.3 |
| Erionic acid D (4) | 374 | 15.4-16.5 |
| Erionic acid E (5) | 374 | 17.0-17.7 |
| Erionic acid F (6) | 358 | 22.0-23.0 |

HTLC Conditions:

| | |
|---|---|
| Pumps: | 2 SunChrom HPLC pumps SunFlow 100 (SunChrom, Friedrichsdorf, Germany) |
| Injector: | 100 μl loop; Midas, Spark, AJ Emmen, The Netherlands |
| HPLC oven: | Polaratherm Series 9000 (Selerity Technologies Inc., Salt Lake City, USA) |
| Detectors: | Light scattering detector (ELSD) Sedex 85 LT-ELSD (Sedere, Alfortville, Cedex, France) |
| | Diode array detector (DAD) SunChrom SpectraFlow, wavelengths 200-400 nm (SunChrom, Friedrichsdorf, Germany) |
| Column: | Hamilton PRP-1 reversed phase; 250 × 10 mm semi-preparative; 10 μm particle size (Hamilton, Bonaduz, Switzerland) |
| Flow rate: | 3 ml/min |
| Fraction collector: | Labocol Vario 2000 (Labomatic, Weil am Rhein) |
| Software: | PrepCon (SCPA GmbH, Weye-Leeste); Version 5.03.009, SCPA GmbH 2003 |
| Stock solution: | 400 mg/ml *E. angustifolium* extract (Y) in ethanol/water (1:1) |
| Injection volume: | 100 μl |
| Column: | Hamilton PRP-1 250 × 10 mm |
| Temperature: | 120° C. isothermal |
| Eluent: | A: water C: ethanol |
| Gradient: | 0 min: 100% A 0% C |
| | 30 min: 50% A 50% C |
| | 50 min: 0% A 100% C |
| | 60 min: 0% A 100% C |
| Detection: | ELSD (3.5 bar N2, 45° C., gain 6); DAD 210 nm, 250 nm, 280 nm, 320 nm |

Analytical Data:

The analytical data for erionic acid C (3) and erionic acid F (6) correspond to those stated in Example 2.

| | Erionic acid D (4) (400 MHz, CH3OD) | | Erionic acid E (5) (400 MHz, CH$_3$OD) | |
|---|---|---|---|---|
| Pos. | $\delta_c$, mult. | $\delta_H$ (J in Hz) | $\delta_c$, mult. | $\delta_H$ (J in Hz) |
| 1 | 130.6$^a$ | | 123.3 | |
| 2 | 130.6$^a$ | 7.60, d (2.2) | 131.0$^a$ | 7.60, d (2.2) |
| 3 | 130.6$^a$ | | 130.3 | |
| 4 | 156.2 | | 158.1 | |
| 5 | 120.9/120.8 | | 128.9 | |
| 6 | 131.3 | 7.61, d (2.2) | 130.8$^a$ | 7.63, d (2.2) |
| 7 | 171.0 | | 171.5 | |
| 8 | 28.9/28.8 | 2.56, m | 29.3 | 2.62, m |
| 9 | 34.0/34.0 | 1.94, m | 34.4 | 1.97, m |
|   |           | 1.60, m |      | 1.63, m |
| 10 | 46.3/46.3 | 2.63, m | 44.5 | 2.89, ddq (6.9, 6.9, 6.9) |
| 11 | 215.6/215.5 | | 207.1 | |
| 12 | 41.9 | 3.17, m | 125.8 | 6.34, d (15.9) |
| 13 | 117.3 | 5.23, m | 155.5 | 6.88, d (15.9) |
| 14 | 136.6 | | 71.2 | |
| 15 | 25.9 | 1.72, s | 29.3 | 1.31, s |
| 16 | 16.7 | 1.11, d (6.9) | 17.2 | 1.15, d (7.0) |
| 17 | 18.3 | 1.60, s | 29.3 | 1.31, s |
| 18 | 32.2 | 3.05/3.06, dd/dd (16.7, 5.2) 2.76, dd (16.6, 7.2) | 29.7 | 3.31 (masked by solvents), |
| 19 | 70.0/70.0 | 3.78, m | 123.4 | 5.33, dd (7.4, 7.4) |
| 20 | 79.1/79.1 | | 134.5 | |
| 21 | 26.1/26.0$^b$ | 1.37/1.36$^a$ | 26.2 | 1.77, s |
| 22 | 21.6/21.3$^b$ | 1.30/1.29$^a$ | 18.0 | 1.71, s |

$^{a,b}$interchangeable signals

Example 4

Production of a Concentrated Extract from *E. angustifolium* by Means of Gel Permeation Chromatography From 0.5 g of the methanolic extract of *E. angustifolium* according to Example 1, the flavanones were removed with a flow rate of 2.5 ml/min over a Sephadex-LH 20 column, and the remaining extract dried under vacuum and stored overnight in the high vacuum drying oven to remove residual solvent. The flavonoid-free dry extract thus obtained had a content of 46% of benzoic acid derivatives to be used according to the invention.

Gel Permeation Chromatography Conditions:

Stock solution: 0.5 g/20 ml methanol

Column: Kronlab 3.5×60 cm

Column material: Sephadex LH-20

Solvent: Methanol

Flow rate: 2.5 ml/min

Detection (UV): 210 nm

Example 5

Production of a Methanolic Extract from *Eriodictyon californicum*

Boiling water was poured over 150 g of dried leaves of *Eriodictyon californicum* and stirred for one hour in order to swell the plant material and prepare it for the further extraction. The plant material was filtered off, dried and extracted twice with 1.5 l of methanol each time at room temperature for one hour with stirring. The extract was filtered, dried under vacuum and stored overnight in the high vacuum drying oven to remove residual solvent. The extraction yielded 32.65 g of dark green extract.

Example 6

Isolation of the Individual Compounds from *Eriodictyon californicum* by Means of HTLC The methanolic extract of *E. californicum* according to Example 5 was separated and fractionated by means of HTLC using a polymer-based semi-preparative column with water-ethanol gradients under isothermal conditions (120° C.). In addition to flavones known from the literature, four compounds of the formula (X) could be isolated.

| Compound | Molecular weight [g/mol] | Retention time [mins] |
|---|---|---|
| Eriolic acid A (7) | 388 | 15.0-16.5 |
| Eriolic acid B (8) | 358 | 21.0-22.9 |
| Eriolic acid C (9) | 374 | 13.5-14.8 |
| Eriolic acid D (10) | 372 | 20.0-21.0 |

HTLC Conditions:

| | |
|---|---|
| Pumps: | 2 SunChrom HPLC pumps SunFlow 100 (SunChrom, Friedrichsdorf, Germany) |
| Injector: | 100 μl loop; Midas, Spark, AJ Emmen, The Netherlands |
| HPLC oven: | Polaratherm Series 9000 (Selerity Technologies Inc., Salt Lake City, USA) |
| Detectors: | Light scattering detector (ELSD) Sedex 85 LT-ELSD (Sedere, Alfortville, Cedex, France) |
| | Diode array detector (DAD) SunChrom SpectraFlow, wavelengths 200-400 nm (SunChrom, Friedrichsdorf, Germany) |
| Column: | Hamilton PRP-1 reversed phase; 250 × 10 mm semi-preparative; 10 μm particle size (Hamilton, Bonaduz, Switzerland) |
| Flow rate: | 3 ml/min |
| Fraction collector: | Labocol Vario 2000 (Labomatic, Weil am Rhein) |
| Software: | PrepCon (SCPA GmbH, Weye-Leeste); Version 5.03.009, SCPA GmbH 2003 |
| Stock solution: | 300 mg/ml *E. californicum* extract (Y) in ethanol/water (1:1) |
| Injection volume: | 100 μl |
| Column: | Hamilton PRP-1 250 × 10 mm |
| Temperature: | 120° C. isothermal |
| Eluent: | A: water C: ethanol |
| Gradient: | 0 min: 100% A 0% C |
| | 30 min: 50% A 50% C |
| | 50 min: 0% A 100% C |
| | 60 min: 0% A 100% C |
| Detection: | ELSD (3.5 bar N2, 45° C., gain 6); DAD 210 nm, 250 nm, 280 nm, 320 nm |

Analytical Data:

| Pos. | $\delta_c$, mult. | $\delta_H$ (J in Hz) | $\delta_c$, mult. | $\delta_H$ (J in Hz) |
|---|---|---|---|---|
| | Eriolic acid A (7) (400 MHz, CH3OD) | | Eriolic acid B (8) (400 MHz, CH$_3$OD) | |
| 1 | 129.6 | | 123.1 | |
| 2 | 131.0 | 7.72, s | 130.3 | 7.64, d (2.2) |
| 3 | 135.7 | | 128.8 | |
| 4 | 161.4 | | 158.2 | |
| 5 | 135.7 | | 129.2 | |
| 6 | 130.9 | 7.72, s | 130.3 | 7.63, d (2.2) |
| 7 | 170.6 | | 170.9 | |
| 8 | 28.8$^b$ | 3.43, d (7.1) | 29.0 | 3.38, d (7.4) |
| 9 | 125.5 | 5.50, dd (7.2, 7.2) | 124.9 | 5.50, dd (7.4, 7.4) |
| 10 | 139.6 | | 139.6 | |
| 11 | 78.6 | 3.98, dd (7.0, 7.0) | 78.7 | 3.99, dd (7.0, 7.0) |
| 12 | 34.8 | 2.26, dd (7.0, 7.0) | 34.8 | 2.26, dd (7.0, 7.0) |
| 13 | 121.7 | 5.07, dd (7.0, 7.0) | 121.7 | 5.08, dd (7.0, 7.0) |
| 14 | 134.0 | | 134.0 | |
| 15 | 26.0 | 1.63, s | 26.0 | 1.64, s |
| 16 | 11.8 | 1.74, s | 11.6 | 1.72, s |
| 17 | 18.0 | 1.60, s | 17.9$^a$ | 1.59, s |
| 18 | 28.9$^a$ | 3.45, d (7.1) | 29.4 | 3.33, d (7.1) |
| 19 | 124.5 | 5.57, dd (7.3, 7.3) | 123.0 | 5.32, dd (7.3, 7.3) |
| 20 | 137.5 | | 134.1 | |
| 21 | 68.7 | 3.98, s | 26.0 | 1.76, s |
| 22 | 13.9 | 1.78, s | 18.0$^a$ | 1.72, s |
| 23 | 61.6 | | | |
| | Eriolic acid C (9) (400 MHz, CH3OD) | | Eriolic acid D (10) (400 MHz, CH$_3$OD) | |
| 1 | 123.4 | | 128.4 | |
| 2 | 130.4 | 7.65, s | 130.8 | 7.71, d (2.2) |
| 3 | 128.8 | | 135.5 | |
| 4 | 158.1 | | 161.3 | |
| 5 | 128.8 | | 136.1 | |
| 6 | 130.4 | 7.65, s | 130.8 | 7.70, d (2.2) |
| 7 | 171.1 | | 170.7 | |
| 8 | 29.1$^a$ | 3.38, d (7.2) | 28.8 | 3.43, d (7.3) |
| 9 | 124.7 | 5.55, dd (7.4, 7.4) | 125.5 | 5.50, dd (7.2, 7.2) |
| 10 | 139.6 | | 139.5 | |
| 11 | 78.6 | 3.99, dd (7.1, 7.1) | 78.6 | 3.98, dd (7.0, 7.0) |
| 12 | 34.8 | 2.26, dd (7.1, 7.1) | 34.8 | 2.26, dd (7.0, 7.0) |
| 13 | 121.6 | 5.09, dd (7.1, 7.1) | 121.6 | 5.06, dd (7.0, 7.0) |
| 14 | 134.0 | | 133.9 | |
| 15 | 26.0 | 1.64, s | 26.0$^a$ | 1.63, s |
| 16 | 11.6 | 1.72, s | 11.7 | 1.74, s |
| 17 | 18.0 | 1.60, s | 18.0$^b$ | 1.59, s |
| 18 | 28.9$^a$ | 3.40, d (7.4) | 29.2 | 3.38, d (7.3) |
| 19 | 124.1 | 5.61, dd (7.4, 7.4) | 123.7 | 5.28, dd (7.3, 7.3) |
| 20 | 137.4 | | 133.9 | |
| 21 | 68.8 | 3.99, s | 25.9$^a$ | 1.75, s |
| 22 | 13.8 | 1.76, s | 17.9$^b$ | 1.74, s |
| 23 | | | 61.5 | 3.76, s |

$^{a,b}$interchangeable signals

Example 7

Production of a Concentrated Extract from *Eriodictyon californicum* by Means of Precipitation 5.0 g of an extract of *E. californicum* prepared analogously to Example 5 were dissolved in 100 ml ethyl acetate. By addition of 10 ml of 3% sodium hydroxide solution with stirring, the homoeriodictyol contained was precipitated out. The remaining solution was dried over sodium sulphate and concentrated. The sterubin also contained in the extract was precipitated out by storage of the extract in the refrigerator for 12 hours. After filtration, the filtrate was dried under vacuum and stored overnight in the high vacuum drying oven to remove residual solvent. The flavonoid-depleted dry extract thus obtained contained benzoic acid derivatives to be used according to the invention in a proportion of 50%.

Example 8

Production of a Concentrated Extract from *E. Californicum* by Means of Gel Permeation Chromatography From 0.5 g of the methanolic extract of *E. californicum* according to Example 5, the flavanoids were removed with a flow rate of 2.5 ml/min over a Sephadex-LH 20 column, and the remaining extract dried under vacuum and stored overnight in the high vacuum drying oven to remove residual solvent. The purified dry extract thus obtained had a content of the benzoic acid derivates to be used according to the invention of 75%.

Stock solution: 0.5 g/20 ml methanol
Column: Kronlab 3.5×60 cm
Column material: Sephadex LH-20
Solvent: Methanol
Flow rate: 2.5 ml/min
Detection (UV): 210 nm

Example 9

Production of a Concentrated Extract by Means of Gel Permeation Chromatography An extract prepared according to WO2004041804 which had already been depleted of homoeriodictyol and sterubin by the method described therein was fractionated over a Sephadex LH-20 column analogously to Example 4 to remove the residual flavonoids, dried under vacuum and stored overnight in the high vacuum drying oven to remove residual solvent. The flavanoid-free dry extract thus obtained had a content of the benzoic acid derivatives to be used according to the invention of 62%.

USE EXAMPLES

Use Example 1

Low-Fat Yoghurt, Sweetened

| Ingredient | Preparation (data in wt. %) | | |
|---|---|---|---|
| | A | B | C |
| Sucrose | 10% | 8% | 6% |
| Tagatose | — | — | 0.5% |
| Fructose | — | — | 0.05% |
| Hesperetin | — | 0.1% | 0.005% |
| Phloretin | — | — | 0.005% |
| Strawberry flavour | — | 0.25% | — |
| Peach flavour | 0.3% | — | 0.4% |
| Herba Santa extract (*E. angustifolium*) as per Example 1 (10% in ethanol) | 0.4% | 0.4% | |
| Concentrated Herba Santa extract (*E. angustifolium*) as per Ex. 4 (10% in ethanol) | | | 0.1% |
| Yoghurt, 0.1% fat | q.s.p. 100% | q.s.p. 100% | q.s.p. 100% |

Use Example 2

Low Fat Yoghurt, Reduced Sugar

| Ingredient | Preparation (data in wt. %) | | | |
|---|---|---|---|---|
| | A | B | C | D |
| Tagatose | 0.482% | 0.482% | 0.482% | |
| Sucralose | 0.003% | 0.003% | 0.003% | |
| Aspartame | 0.005% | 0.005% | 0.005% | |
| Acesulfam K | 0.01% | 0.01% | 0.01% | |
| Rebaudioside A | | | | 0.005% |
| *Rubus suavissimus* extract | | | | 0.005% |
| Hesperetin | | 0.01% | 0.005% | 0.005% |
| Phloretin | — | — | 0.005% | 0.005% |
| Strawberry flavour | — | 0.25% | — | 0.25% |
| Raspberry flavour | 0.3% | — | 0.4% | |
| Herba Santa extract (*E. californicum*) as per Ex. 5 (10% in ethanol) | 0.5% | | | 0.4% |
| Concentrated Herba Santa extract (*E. californicum*) as per Ex. 8 (10% in ethanol) | | 0.1% | 0.1% | |
| Yoghurt, 0.1% fat | q.s.p. 100% | q.s.p. 100% | q.s.p. 100% | q.s.p. 100% |

Use Example 3

Low Fat Yoghurt Drink, Sweetened

| Ingredient | Preparation (data in wt. %) | | |
|---|---|---|---|
| | A | B | C |
| Sucrose | 7% | 4% | 5% |
| Tagatose | — | — | 0.5% |
| Fructose | — | — | 0.05% |
| Hesperetin | — | 0.1% | 0.005% |
| Phloretin | — | — | 0.005% |
| Strawberry flavour | — | 0.15% | — |
| Red fruit flavour | 0.2% | — | 0.25% |
| Colouring food: fruit juice | 5% | 5% | 5% |
| Herba Santa extract (*E. angustifolium*) as per Example 1 (10% in ethanol) | 0.35% | 0.2% | |
| Concentrated Herba Santa extract (*E. angustifolium*) as per Ex. 4 (10% in ethanol) | | | 0.15% |
| Yoghurt, 0.1% fat | 60% | 60% | 60% |
| Water | q.s.p. 100% | q.s.p. 100% | q.s.p. 100% |

Use Example 4

Sugar-Free Hard Caramels

| Ingredient | A (wt. %) | A (wt. %) |
|---|---|---|
| Palatinit, type M | q.s.p. 100% | q.s.p. 100% |
| Water | 24.82% | 24.82% |
| Peppermint flavour | 0.15% | 0.05% |
| Hesperetin | | 0.10% |
| Trans-pellitorin (10% in ethanol) | 0.01% | |
| Herba Santa extract (*E. angustifolium*) as per Ex. 1 (10% in ethanol) | 0.1% | |
| Concentrated Herba Santa extract (*E. angustifolium*) as per Ex. 4 (10% in ethanol) | | 0.05% |

Palatinit was mixed with water and the mixture was melted at 165° C. then cooled to 115° C. Flavouring and extract produced according to the invention, and trans-pellitorin in case A and hesperetin in case B, were added, and after thorough mixing poured into moulds, and after solidification were removed from the foil and then individually packed.

Use Example 5

Black, Green or Herb Tea

| | Proportion in weight % | | | | |
|---|---|---|---|---|---|
| Ingredient | A | B | C | D | E |
| Black tea (Ceylon) leaves | 99.4 | — | — | — | — |
| Green tea (China), leaves | — | 99.2 | — | — | — |
| Mate tea (Peru), leaves | — | — | 99.5 | — | — |
| Rooibos tea (South Africa), leaves | — | — | — | 99.6 | — |
| Honeybush tea (South Africa), leaves | — | — | — | — | 99.6 |
| Herba Santa extract (*E. angustifolium*) as per Ex. 1 | 0.3 | 0.8 | — | 0.4 | 0.2 |
| Herba Santa extract (*E. californicum*) as per Ex. 5 | 0.3 | — | 0.5 | — | 0.2 |

Use Example 6

Soya Drink

| | Preparation (data in wt. %) | | |
|---|---|---|---|
| Ingredient | A | B | C |
| Sucrose | 5% | 5% | 3.5% |
| Tagatose | — | — | 0.5% |
| Fructose | — | — | 0.05% |
| Hesperetin | — | — | 0.005% |
| Phloretin | — | — | 0.005% |
| Chocolate flavour | — | 0.15% | — |
| Vanilla flavour | 0.1% | — | 0.1% |
| Herba Santa extract (*E. angustifolium*) as per Example 1 (10% in ethanol) | 0.08% | 0.1% | |
| Concentrated Herba Santa extract (*E. californicum*) as per Ex. 8 (10% in ethanol) | | | 0.05% |
| Unsweetened soya milk base | q.s.p. 100% | q.s.p. 100% | q.s.p. 100% |

Use Example 7

Fruity Muesli Bars

| | |
|---|---|
| Saccharose | 15.992% |
| Glucose syrup | 14.0% |
| Sorbitol P300 | 5.0% |
| Plant fat | 5.0% |
| Water | 3.0% |
| Rolled oats | 7.3% |
| Oat flakes | 7.0% |
| Cornflakes | 4.5% |
| Rice crispies | 15.0% |
| Currants | 3% |
| Dried blueberries | 20% |
| Citric acid powder | 0.2% |
| Concentrated Herba Santa extract as per Ex. 4 | 0.008% |

Use Example 8

Chewing Gum for Bad Breath

| | I (%) | II (%) | III (%) | IV (%) |
|---|---|---|---|---|
| Chewing gum base | 21.00 | 21.00 | 21.00 | 21.00 |
| Glucose syrup | 16.80 | 16.80 | 16.50 | 16.50 |
| Glycerine | 0.50 | 0.50 | 0.50 | 0.50 |
| Sugar powder | 60.00 | 60.00 | 60.40 | 60.40 |
| Spearmint flavour | 1.50 | 1.50 | 1.50 | 1.50 |
| Herba Santa extract (*E. angustifolium*) as per Ex. 1 10% in ethanol | 0.2 | | | |
| Herba Santa extract (*E. californicum*) as per Ex. 5 10% in ethanol | | 0.2 | | |
| Concentrated extract from *E. angustifolium* as per Ex. 4 10% in ethanol | | | 0.1 | |
| Concentrated extract from *E. californicum* as per Ex. 7 10% in ethanol | | | | 0.1 |

Use Example 9

Sugar-Free Chewing Gum for Bad Breath

| | I (%) | II (%) | III (%) | IV (%) |
|---|---|---|---|---|
| Chewing gum base | 30.00 | 30.00 | 30.00 | 30.00 |
| Sorbitol, powder | 38.25 | 38.25 | 38.40 | 38.40 |
| Palatinit | 9.50 | 9.50 | 9.50 | 9.50 |
| Xylitol | 2.00 | 2.00 | 2.00 | 2.00 |
| Mannitol | 3.00 | 3.00 | 3.00 | 3.00 |
| Aspartame | 0.10 | 0.10 | 0.10 | 0.10 |
| Acesulfam K | 0.10 | 0.10 | 0.10 | 0.10 |
| Emulgum/emulsifier | 0.30 | 0.30 | 0.30 | 0.30 |
| Sorbitol 70%, in water | 14.00 | 14.00 | 14.00 | 14.00 |
| Glycerine | 1.00 | 1.00 | 1.00 | 1.00 |
| Cinnamon/menthol flavour | 1.50 | 1.50 | 1.50 | 1.50 |
| Herba Santa extract (*E. angustifolium*) as per Ex. 1 10% in ethanol | 0.25 | | | |
| Herba Santa extract (*E. californicum*) as per Ex. 5 10% in ethanol | | 0.2 | | |
| Concentrated extract from *E. angustifolium* as per Ex. 4 10% in ethanol | | | 0.1 | |
| Concentrated extract from *E. californicum* as per Ex. 7 10% in ethanol | | | | 0.1 |

Use Example 10

Ready-to-Use Mouthwash Solution with Fluoride for Bad Breath

| | I (%) | II (%) | III (%) |
|---|---|---|---|
| Ethanol | 7.00 | 7.00 | 7.00 |
| Glycerine | 12.00 | 12.00 | 12.00 |
| Na fluoride | 0.05 | 0.05 | 0.05 |
| Pluronic F-127 ® (BASF, surface-active substance) | 1.40 | 1.40 | 1.40 |
| Na phosphate buffer pH 7.0 | 1.10 | 1.10 | 1.10 |
| Sorbic acid | 0.20 | 0.20 | 0.20 |

|  | I (%) | II (%) | III (%) |
|---|---|---|---|
| Na saccharinate | 0.10 | 0.10 | 0.10 |
| Cinnamon/menthol flavour | 0.15 | 0.15 | 0.15 |
| Herba Santa extract (*E. angustifolium*) as per Ex. 1 10% in ethanol | 0.3 | | |
| Herba Santa extract (*E. californicum*) as per Ex. 5 10% in ethanol | | 0.3 | |
| Concentrated extract from *E. angustifolium* as per Ex. 4 10% in ethanol | | | 0.08 |
| Colorant | 0.01 | 0.01 | 0.01 |
| Dist. water | to 100.00 | to 100.00 | to 100.00 |

Use Example 11

Mouthwash Solution (Concentrate) for Bad Breath

| Ingredients | I (%) | II (%) | III (%) |
|---|---|---|---|
| Ethanol, 95% | 80.00 | 80.00 | 80.00 |
| Na cyclamate | 0.15 | 0.15 | 0.15 |
| Eucalyptus/wintergreen flavour | 3.50 | 3.50 | 3.50 |
| Colorant | 0.01 | 0.01 | 0.01 |
| Herba Santa extract (*E. angustifolium*) as per Ex. 1 | 0.50 | | |
| Concentrated extract from *E. angustifolium* as per Ex. 4 | | 0.1 | |
| Concentrated extract from *E. californicum* as per Ex. 7 | | | 0.1 |
| Demin. water | q.s.p. 100.00 | q.s.p. 100.00 | q.s.p. 100.00 |

Use Example 12

Mouthwash Solution with Fluoride for Bad Breath

| Ingredient | INCI | Weight % |
|---|---|---|
| Ethyl alcohol | Ethyl alcohol | 10.00 |
| Cremophor CO 40 | Cremophor CO 40 (PEG 40 hydrogenated castor oil) | 1.00 |
| Benzoic acid | Benzoic acid | 0.12 |
| Aroma (PF1, PF2, PF3 or PF4) | Flavour | 0.25 |
| Demin. water | Water (deionized) | 83.28 |
| Sorbitol 70% | Sorbitol 70% | 5.00 |
| Sodium saccharin | Sodium saccharin 450 | 0.07 |
| Sodium fluoride | Sodium fluoride | 0.18 |
| Herba Santa extract (*E. angustifolium*) as per Ex. 1 (10% in ethanol) | | 0.10 |

Use Example 13

Toothpaste

| Ingredient | INCI | Weight % |
|---|---|---|
| Demin. water | Water (deionized) | 26.31 |
| Sorbitol 70% | Sorbitol 70% | Sorbitol 70% |
| Solbrol M (Na salt) | Solbrol M (Sodium salt) (methylparaben) | 0.15 |
| Trisodium phosphate | Trisodium phosphate | 0.10 |
| Saccharin | Saccharin | 0.20 |
| Sodium monofluorophosphate | Sodium monofluorophosphate | 1.14 |
| PEG 1500 | PEG 1500 | 5.00 |
| Sident 9 (abrasive silica gel) | Sident 9 (abrasive silica) | 10.00 |
| Sident 22 S (thickener) | Sident 22 S (thickening silica) | 8.00 |
| Sodium carboxymethylcellulose | Sodium carboxymethyl-cellulose | 1.10 |
| Titanium (IV) oxide | Titanium (IV) oxide | 0.50 |
| Sodium laurylsulphate (SLS) | Sodium laurylsulphate (SLS) | 1.50 |
| Aroma (PF1, PF2, PF3 or PF4) | Flavour | 1.00 |
| Concentrated Herba Santa extract (*E. californicum*) as per Ex. 7 (10% in ethanol) | | 0.40 |

Use Example 14

Anti-Plaque Toothpaste

| Ingredient | Weight % | Weight % |
|---|---|---|
| Carrageenan | 0.90 | 0.90 |
| Glycerol | 15.00 | 15.00 |
| Sorbitol 70%, in water | 25.00 | 25.00 |
| PEG 1000 | 3.00 | 3.00 |
| Na fluoride | 0.24 | 0.24 |
| Tetrapotassium diphosphate | 4.50 | 4.50 |
| Tetrasodium diphosphate | 1.50 | 1.50 |
| Na saccharinate | 0.40 | 0.40 |
| Precipit. silica gel | 20.00 | 20.00 |
| Titanium dioxide | 1.00 | 1.00 |
| Triclosan | 0.30 | 0.30 |
| PHB methyl ester | 0.10 | 0.10 |
| Spearmint flavour (containing 60 wt. % L-carvone and 25 wt. % L-menthol) | 1.00 | 1.20 |
| Concentrated Herba Santa extract (*E. californicum*) as per Ex. 7 (10% in ethanol) | 0.30 | — |
| Herba Santa extract (*E. californicum*) as per Ex. 1 (10% in ethanol) | — | 0.50 |
| Sodium dodecylsulphate | 1.30 | 1.30 |
| Demin. water | q.s.p. 100 | q.s.p. 100 |

Use Example 15

Tooth Cream for Pain-Sensitive Teeth

| Ingredient | Weight % | Weight % |
|---|---|---|
| Na carboxymethylcellulose | 0.70 | 0.70 |
| Xanthan gum | 0.50 | 0.50 |
| Glycerol | 15.00 | 15.00 |
| Sorbitol 70%, in water | 12.00 | 12.00 |
| Potassium nitrate | 5.00 | 5.00 |
| Sodium monofluorophosphate | 0.80 | 0.80 |
| PHB methyl ester | 0.15 | 0.15 |
| PHB propyl ester | 0.05 | 0.05 |
| Na saccharinate | 0.20 | 0.20 |
| Flavour (PF1, PF2, PF3 or PF4) | 1.00 | 1.00 |
| Herba Santa extract (*E. angustifolium*) as per Ex. 1 (10% in ethanol) | 0.50 | — |

-continued

| Ingredient | Weight % | Weight % |
|---|---|---|
| Herba Santa extract (*E. californicum*) as per Ex. 5 (10% in ethanol) | — | 0.25 |
| Ca carbonate | 35.00 | 35.00 |
| Silicon dioxide | 1.00 | 1.00 |
| Sodium dodecylsulphate (SDS) | 1.50 | 1.50 |
| Demin. water | q.s.p. 100.00 | q.s.p. 100.00 |

Use Example 16

Gelatine Capsules for Bad Breath for Direct Consumption

| | I (%) | II (%) | III (%) |
|---|---|---|---|
| Gelatine casing | | | |
| Glycerine | 2.014 | 2.014 | 2.014 |
| Gelatine 240 Bloom | 7.91 | 7.91 | 7.91 |
| Sucralose | 0.065 | 0.065 | 0.065 |
| Allura Red | 0.006 | 0.006 | 0.006 |
| Brilliant Blue | 0.005 | 0.005 | 0.005 |
| Core filling: | | | |
| Plant oil triglycerides | 82.00 | 74.00 | 60.00 |
| Flavour B | 7.9 | 15.50 | 29.5 |
| Herba Santa extract (*E. angustifolium*) as per Ex. 1 (10% in ethanol) | 0.10 | 0.50 | — |
| Herba Santa extract (*E. californicum*) as per Ex. 5 (10% in ethanol) | 0.10 | — | 0.50 |

Flavour B had the following composition (data in weight %): 0.1% neotame (powder), 0.05% aspartame, 29.3% peppermint oil (Avensis), 29.3% peppermint oil (Piperita; Willamette), 2.97% sucralose, 2.28% triacetin, 5.4% diethyl tartrate, 12.1% peppermint oil (Yakima), 0.7% ethanol, 3.36% 2-hydroxyethyl menthyl carbonate, 3.0% 2-hydroxypropyl menthyl carbonate, 0.27% vanillin, 5.5% D-limonene, 5.67% L-menthyl acetate.

The gelatine capsule, which is suitable for direct consumption, has a diameter of 5 mm; the weight ratio between core and casing material is about 90:10. The capsules open in the mouth in less than 10 secs, and dissolve completely within 50 secs.

Use Example 17

Syndet—Soap-Free Cleansing Bar

| Ingredient | INCI Name | Weight % | Weight % |
|---|---|---|---|
| Zetesap 813 A | Disodium lauryl sulphosuccinate, sodium lauryl sulphate, corn starch, cetearyl alcohol, paraffin, titanium dioxide | 92.0 | 91.9 |
| Amphotensid GB 2009 | Disodium cocoamphodiacetate | 6.0 | 6.0 |
| Allantoin | Allantoin | 1.0 | 1.0 |
| Perfume oil P2, P4, P6 or P7 | Fragrance | 1.0 | — |
| Perfume oil P1, P3 or P5 | Fragrance | — | 1.0 |
| Herba Santa extract (*E. angustifolium*) as per Example 1 (10% in ethanol) | 0.5 | — |
| Concentrated Herba Santa extract (*E. angustifolium*) as per Example 4 (10% in ethanol) | — | 0.1 |

Use Example 18

Soap Bar

| Ingredient | INCI | Weight % | Weight % |
|---|---|---|---|
| Demin. water | Water | 2.5 | 2.5 |
| Soap base mix | Sodium tallowates/palmitates | 95.5 | 95.8 |
| Titanium dioxide | Titanium dioxide | 1.0 | 1.0 |
| Perfume oil P2, P4, P6 or P7 | Fragrance | 0.8 | — |
| Perfume oil P1, P3 or P5 | Fragrance | — | 0.5 |
| Concentrated Herba Santa extract (*E. angustifolium*) as per Example 4 (10% in ethanol) | 0.2 | — |
| Concentrated Herba Santa extract (*E. californicum*) as per Example 7 (10% in ethanol) | — | 0.2 |

Use Example 19

Antimicrobial Soap Bar

| Ingredient | Weight % | Weight % |
|---|---|---|
| Sodium soap from tallow | 60.0 | 60.0 |
| Sodium soap from palm oil | 27.0 | 27.0 |
| Glycerol | 2.0 | 2.0 |
| Sodium chloride | 0.5 | 0.5 |
| 1-hydroxyethane-1,1-diphosphoric acid, tetrasodium salt | 0.3 | 0.3 |
| Alpha-tocopherol | 0.1 | 0.1 |
| Pigment yellow 1 | 0.02 | 0.02 |
| Water | q.s.p. 100 | q.s.p. 100 |
| Perfume oil P2, P4, P6 or P7 | 3.0 | — |
| Perfume oil P1, P3 or P5 | — | 3.0 |
| Herba Santa extract (E.) as per Example 1 (10% in ethanol) | 0.5 | — |
| Concentrated Herba Santa extract (*E. angustifolium*) as per Example 7 (10% in ethanol) | — | 0.2 |

Use Example 20

Liquid Soap

| Ingredient | INCI Name | Weight % | Weight % |
|---|---|---|---|
| Tagat O 2 | PEG-20 Glyceryl oleate | 2.5 | 2.5 |
| Coconut fatty acid diethanolamide | Cocamide DEA | 5.0 | 5.0 |
| Abil B 8842 | Cyclomethicone | 0.5 | 0.5 |
| Sodium laurylether sulphate, 28% | Sodium laureth sulphate | 35.0 | 35.0 |

-continued

| Ingredient | INCI Name | Weight % | Weight % |
| --- | --- | --- | --- |
| Tego-betaine L7 | Cocamidopropyl betaine | 5.0 | 5.0 |
| Soap, 25% | Coconut acid, potassium salt, potassium oleate | 20.0 | 20.0 |
| Water | Water | q.s.p. 100 | q.s.p. 100 |
| Preservative | DMDM hydantoin | | |
| Perfume oil P2, P4, P6 or P7 | Fragrance | 0.4 | — |
| Perfume oil P1, P3 or P5 | Fragrance | — | 0.4 |
| Concentrated Herba Santa extract (*E. angustifolium*) as per Ex. 4 (10% in ethanol) | | 0.4 | 0.3 |

Use Example 21

Liquid Soap (Syndet)

| Ingredients | INCI Name | Weight % | Weight % |
| --- | --- | --- | --- |
| Elfan OS 46 | Sodium olefin C14-C16 sulphonate | 35.5 | 35.5 |
| Armoteric LB | Lauryl betaine | 8.0 | 8.0 |
| Elfan SG | | 10.0 | 10.0 |
| Elfacos GT 282 L | Talloweth-60 myristyl glycol | 3.0 | 3.0 |
| PCL-Liquid 100 | cetearyl ethylhexanoate | 4.0 | 4.0 |
| Water | water | q.s.p. 100 | q.s.p. 100 |
| Preservative | methylchloroisothiazolinone, methylisothiazinone | | |
| Perfume oil P2, P4, P6 or P7 | Fragrance | 0.4 | — |
| Perfume oil P1, P3 or P5 | Fragrance | — | 0.4 |
| Herba Santa extract (*E. angustifolium*) as per Ex. 1 (10% in ethanol) | | 0.5 | |
| Herba Santa extract (*E. californicum*) as per Ex. 5 (10% in ethanol) | | | 0.3 |

Use Example 22

Shampoo

| Ingredients | Weight % | Weight % |
| --- | --- | --- |
| Sodium lauryl ether sulphate (e.g. Texapon NSO) | 12 | 12 |
| Cocamidopropylbetaine (e.g. Dehyton K) | 2 | 2 |
| Sodium chloride | 1.4 | 1.4 |
| Citric acid | 1.3 | 1.3 |
| Phenoxyethanol, methyl, ethyl, butyl and propylparaben | 0.5 | 0.5 |
| Perfume oil P2, P4, P6 or P7 | 0.3 | — |
| Perfume oil P1, P3 or P5 | — | 0.3 |
| Herba Santa extract (*E. californicum*) as per Ex. 5 (10% in ethanol) | 0.25 | — |
| Herba Santa extract (*E. californicum*) as per Ex. 7 (10% in ethanol) | | 0.15 |
| Water | q.s.p. 100 | q.s.p. 100 |

Use Example 23

2 in 1-Shampoo

| Ingredients | INCI Name | Weight % | Weight % |
| --- | --- | --- | --- |
| Demineralized water | Water | q.s.p. 100 | q.s.p. 100 |
| Plantacare PS 10 | Sodium laureth sulphate, lauryl glucoside | 20.0 | 20.0 |
| Euperlan PK 771 | Glycol distearate, sodium lauryl sulphate, cocamide MEA, laureth-10 | 6.0 | 6.0 |
| Dragocid liquid | Phenoxyethanol, methylparaben, ethylparaben, butylparaben, propylparaben, isobutylparaben | 0.5 | 0.5 |
| Sodium chloride | Sodium chloride | 1.4 | 1.4 |
| Citric acid monohydrate (crystalline) | Citric acid | 0.1 | 0.1 |
| Perfume oil P2, P4, P6 or P7 | Fragrance | 0.5 | — |
| Perfume oil P1, P3 or P5 | Fragrance | — | 0.5 |
| Concentrated Herba Santa extract (*E. angustifolium*) as per Ex. 4 (10% in ethanol) | | 0.15 | — |
| Herba Santa extract (*E. californicum*) as per Ex. 8 (10% in ethanol) | | — | 0.15 |

Use Example 24

Anti-Dandruff Shampoo

| Ingredients | (INCI Name) | Weight % | Weight % |
| --- | --- | --- | --- |
| Climbazole | Climbazole | 0.50 | 0.50 |
| Phenoxyethanol, methylparaben, Ethylparaben, Butylparaben, Propylparaben, Isobutylparaben | Phenoxyethanol, methylparaben, ethylparaben, butylparaben, propylparaben, isobutylparaben | 0.70 | 0.70 |
| Herba Santa extract (*E. angustifolium*) as per Ex. 1 (10% in ethanol) | | 0.60 | — |
| Concentrated Herba Santa extract (*E. angustifolium*) as per Ex. 4 (10% in ethanol) | | — | 0.40 |
| Sodium laureth sulphate | Sodium laureth sulphate | 37.00 | 37.00 |
| Cocamidopropyl betaine | Cocamidopropyl betaine | 8.00 | 8.00 |
| PEG-6 | PEG-6 caprylic/capric glycerides | 2.50 | 2.50 |
| Laureth-2 | Laureth-2 | 2.00 | 2.00 |
| Thyme extract | Water (aqua), glycerol, *Thymus vulgaris* (thyme), flower/leaf extract | 0.50 | 0.50 |
| Rosemary extract | *Rosmarinus officinalis* (rosemary) leaf water, water (aqua), butylene glycol, pentylene glycol | 0.50 | 0.50 |
| Bisabolol | Bisabolol | 0.10 | 0.10 |
| Panthenol | Panthenol | 0.50 | 0.50 |
| Perfume oil P2, P4, P6 or P7 | Fragrance | 0.50 | — |
| Perfume oil P1, P3 or P5 | Fragrance | — | 0.50 |
| Water | Water (aqua) | 46.30 | 46.30 |
| Polyquaternium-10 | Polyquaternium-10 | 0.40 | 0.40 |

Use Example 25

Shower Gel

| Ingredients | INCI | Weight % | Weight % |
|---|---|---|---|
| Demin. water | Water | q.s.p. 100 | q.s.p. 100 |
| Plantacare PS 10 | Sodium laureth sulphate, lauryl glucoside | 20.0 | 20.0 |
| Dragocid Liquid | Phenoxyethanol, methylparaben, ethylparaben, butylparaben, propylparaben, isobutylparaben | 0.5 | 0.5 |
| Sodium chloride | Sodium chloride | 1.4 | 1.4 |
| Citric acid monohydrate (crystalline) | Citric acid | 1.3 | 1.3 |
| Perfume oil P2, P4, P6 or P7 | Fragrance | 0.6 | — |
| Perfume oil P1, P3 or P5 | Fragrance | — | 0.6 |
| Herba Santa extract (*E. angustifolium*) as per Example 1 (10% in ethanol) | | 0.1 | — |
| Concentrated Herba Santa extract (*E. angustifolium*) as per Example 4 (10% in ethanol) | | — | 0.05 |

Use Example 26

Shaving Foam

| Ingredients | Weight % | Weight % |
|---|---|---|
| Demin. water | 77.2 | 77.22 |
| Triethanolamine | 4.0 | 4.0 |
| Edenor L2 SM (stearic acid, palmitic acid) (Cognis) | 5.3 | 5.3 |
| Laureth-23 | 3.0 | 3.0 |
| Stearyl alcohol | 0.5 | 0.5 |
| euxyl ® K220 (methylisothiazolinone, ethylhexylglycerol) | 0.8 | 0.8 |
| Sodium lauryl sulphate | 3.0 | 3.0 |
| Extrapone seaweed/alga (water, propylene glycol, potassium iodide, *Fucus Vesiculosus* Extract) | 1.0 | 1.0 |
| Dragosantol (bisabolol, farnesol) | 0.1 | 0.1 |
| Perfume oil P2, P4, P6 or P7 | 1.0 | — |
| Perfume oil P1, P3 or P5 | — | 1 |
| Herba Santa extract (*E. californicum*) as per Example 5 (10% in ethanol) | 0.1 | — |
| Concentrated Herba Santa extract (*E. californicum*) as per Example 8 (10% in ethanol) | — | 0.08 |
| Propane, butane 4.2 bar | 4.0 | 4.0 |

Use Example 27

Aftershave

| Ingredients | INCI | Weight % | Weight % |
|---|---|---|---|
| SymSol ® PF-3 | Water (aqua), pentylene glycol, sodium lauryl sulphoacetate, sodium oleoyl sarcosinate, sodium chloride, disodium sulphoacetate, sodium oleate, sodium sulphate | 3.00 | 3.00 |
| SymSitive ® 1609 | Pentylene glycol, 4-t-butylcyclo-hexanol | 1.00 | 1.00 |
| Frescolat ® ML | Menthyl lactate | 0.30 | 0.30 |
| Glycerol 99.5 P. | Glycerol | 5.00 | 5.00 |
| Water | Water (aqua) | q.s.p. 100 | q.s.p. 100 |
| Extrapone ® Glacier Water GW | Glycerol, Water (aqua) | 1.00 | 1.00 |
| SymCalmin ® | Butylene glycol, pentylene glycol, hydroxyphenyl propamidobenzoic acid | 0.50 | 0.50 |
| Dragosine ® | Carnosine | 0.10 | 0.10 |
| Hydrolite ® 5 | Pentylene glycol | 5.00 | 5.00 |
| Ethanol 96% | Alcohol denat. | 5.00 | 5.00 |
| Colour pigment | Colour pigment | 0.05 | 0.05 |
| Perfume oil P2, P4, P6 or P7 | Perfume | 0.15 | — |
| Perfume oil P1, P3 or P5 | Perfume | — | 0.15 |
| Herba Santa extract (*E. angustifolium*) as per Example 1 (10% in ethanol) | | 0.15 | — |
| Concentrated Herba Santa extract (*E. angustifolium*) as per Example 4 (10% in ethanol) | | — | 0.08 |

Use Example 28

Deodorant Formulation (Roll-on Gel)

| Ingredients | Weight % | Weight % |
|---|---|---|
| 1,3-Butylene glycol | 2.00 | 2.00 |
| PEG-40-hydrogen. castor oil | 2.00 | 2.00 |
| Hydroxyethylcellulose | 0.50 | 0.50 |
| Preservative (phenoxyethanol) | 0.30 | 0.30 |
| Perfume oil P2, P4, P6 or P7 | 0.30 | — |
| Perfume oil P1, P3 or P5 | — | 0.30 |
| Herba Santa extract (*E. angustifolium*) as per Example 1 (10% in ethanol) | 0.30 | — |
| Concentrated Herba Santa extract (*E. angustifolium*) as per Example 4 (10% in ethanol) | — | 0.10 |
| Water | q.s.p. 100.00 | q.s.p. 100.00 |

Use Example 29

Deodorant Stick

| Ingredients | Weight % | Weight % |
|---|---|---|
| Sodium stearate | 8.00 | 8.00 |
| PPG-3 myristyl ether | 70.00 | 70.00 |
| 1,2-propylene glycol | 10.00 | 10.00 |
| 1,1-dimethyl-3-phenylpropanol | 0.20 | 0.25 |
| 2-butyloctanoic acid | 0.20 | 0.20 |
| Perfume oil P2, P4, P6 or P7 | 0.60 | — |
| Perfume oil P1, P3 or P5 | — | 0.60 |
| Herba Santa extract (*E. angustifolium*) as per Example 1 (10% in ethanol) | 0.30 | — |
| Concentrated Herba Santa extract (*E. californicum*) as per Example 7 (10% in ethanol) | — | 0.20 |
| Water | q.s.p. 100 | q.s.p. 100 |

Use Example 30

Antiperspirants

| Ingredients | Weight % | Weight % |
|---|---|---|
| Reach AZP-908 SUF | 24.00 | 22.00 |
| Cyclomethicone (pentamer) | q.s.p. 100 | q.s.p. 100 |
| Polydecene (Silkflo 364 NF) | 17.50 | 20.00 |
| Neo Heliopan OS (ethylhexyl salicylate) | 2.50 | 1.00 |
| L-menthyl lactate (Frescolate ML) | 0.25 | — |
| Polyethylene | 3.00 | 3.00 |
| Hydrogen. castor oil | 2.00 | 2.00 |
| Promyristyl PM-3 | 7.00 | 7.00 |
| PEG-8 distearate | 3.00 | 3.00 |
| Silicon dioxide (Cab-O-Sil M-5) | 1.00 | 1.00 |
| Stearyl alcohol | 15.00 | 10.00 |
| Octyldodecanol | — | 8.00 |
| Perfume oil P2, P4, P6 or P7 | 0.80 | — |
| Perfume oil P1, P3 or P5 | — | 0.80 |
| Herba Santa extract (*E. angustifolium*) as per Example 1 (10% in ethanol) | 0.30 | — |
| Concentrated Herba Santa extract (*E. angustifolium*) as per Example 4 (10% in ethanol) | — | 0.30 |

Use Example 31

O/W Lotion

| Ingredients | INCI | Weight % | Weight % |
|---|---|---|---|
| Paraffin oil | Paraffin oil | 5.00 | 5.00 |
| Isopropyl palmitate | Isopropyl palmitate | 5.00 | 5.00 |
| Cetyl alcohol | Cetyl alcohol | 2.00 | 2.00 |
| Beeswax | Beeswax | 2.00 | 2.00 |
| Ceteareth-20 | Ceteareth-20 | 2.00 | 2.00 |
| PEG-20 glyceryl stearate | PEG-20 glyceryl stearate | 1.50 | 1.50 |
| Glycerol | Glycerol | 3.00 | 3.00 |
| Perfume oil P2, P4, P6 or P7 | Perfume | 0.30 | — |
| Perfume oil P1, P3 or P5 | Perfume | — | 0.30 |
| Herba Santa extract (*E. californicum*) as per Example 5 (10% in ethanol) | | 0.25 | — |
| Concentrated Herba Santa extract (*E. californicum*) as per Example 7 (10% in ethanol) | | — | 0.10 |
| Methylparaben | Methylparabens | 0.30 | 0.30 |
| Water | Water | q.s.p. 100.00 | q.s.p. 100.00 |

Use Example 32

Body Lotion

| Ingredients | INCI | Weight % | Weight % |
|---|---|---|---|
| Cetearyl alcohol | Cetearyl alcohol | 2.00 | 2.00 |
| Ethylhexyl isononanoate | Ethylhexyl isononanoate | 5.00 | 5.00 |
| Cetearyl ethylhexanoate, isopropyl myristate | Cetearyl ethylhexanoate, isopropyl myristate | 3.00 | 3.00 |
| Glyceryl oleate citrate, caprylic/capric triglyceride | Glyceryl oleate citrate, caprylic/capric triglyceride | 4.00 | 4.00 |
| Water | Water (aqua) | 79.50 | 79.50 |
| Carbomer | Carbomer | 0.30 | 0.30 |
| Sodium benzoate | Sodium benzoate | 0.10 | 0.10 |
| Propylene glycol | Propylene glycol | 5.00 | 5.00 |
| Triethylene glycol, imidazolidinylurea, methylparaben, propylparaben, dehydroacetic acid | Triethylene glycol, imidazolidinylurea, methylparaben, propylparaben, dehydroacetic acid | 0.30 | 0.30 |
| Sodium hydroxide Soln. (30%) | Sodium hydroxide 30% solution | 0.30 | 0.30 |
| Perfume oil P2, P4, P6 or P7 | Perfume | 0.30 | — |
| Perfume oil P1, P3 or P5 | Perfume | — | 0.30 |
| Herba Santa extract (*E. angustifolium*) as per Example 1 (10% in ethanol) | | 0.10 | — |
| Herba Santa extract (*E. californicum*) as per Example 5 (10% in ethanol) | | — | 0.10 |

Use Example 32

Hand and Body Cream

| Ingredients | INCI | Weight % | Weight % |
|---|---|---|---|
| Dracorin ® GOC | Glyceryl oleate citrate, caprylic/capric triglycerides | 2.00 | 2.00 |
| PCL-Solid | Stearyl heptanoate, stearyl caprylate | 2.50 | 2.50 |
| Lanette ® O | Cetearyl alcohol | 1.50 | 1.50 |
| Cutina ® GMS-V | Glyceryl stearate | 1.00 | 1.00 |
| Dragoxat ® 89 | Ethylhexyl isononanoate | 3.00 | 3.00 |
| PCL-Liquid 100 | Cetearyl ethylhexanoate | 7.00 | 7.00 |
| Isodragol ® | Triisononanoin | 4.00 | 4.00 |
| Xiameter ® PMX-0345 Cyclosiloxane | Cyclopentasiloxane (and) cyclohexasiloxane | 0.50 | 0.50 |
| Water | Water (aqua) | q.s.p. 100 | q.s.p. 100 |
| Carbopol ® Ultrez 21 | Acrylates/C10-30 alkyl acrylate crosspolymer | 0.20 | 0.20 |
| Keltrol ® CG-RD | Xanthan gum | 0.10 | 0.10 |
| Glycerol 85 P. | Glycerol | 3.00 | 3.00 |
| DragoBetaGlucan | Water (aqua), butylene glycol, glycerol, *Avena sativa* (oat) kernel extract | 1.50 | 1.50 |
| Potassium sorbate | Potassium sorbate | 0.10 | 0.10 |
| euxyl ® K300 | Methyl, butyl, ethyl, propyl, isobutylparaben, phenoxyethanol. | 0.80 | 0.80 |
| Sodium hydroxide 10% solution | Sodium hydroxide | 0.50 | 0.50 |
| Perfume oil P2, P4, P6 or P7 | Perfume | 0.20 | — |
| Perfume oil P1, P3 or P5 | Perfume | — | 0.20 |
| Herba Santa extract (*E. angustifolium*) as per Example 1 (10% in ethanol) | | 0.20 | — |
| Concentrated Herba Santa extract (*E. angustifolium*) as per Example 4 (10% in ethanol) | | — | 0.15 |

Use Example 33

Face Cream

| Ingredients | INCI | Weight % | Weight % |
|---|---|---|---|
| Emulsiphos ® | Potassium cetyl phosphate, hydrogenated palm glycerides | 1.50 | 1.50 |
| Cutina ® GMS-V | Glyceryl stearate | 1.70 | 1.70 |
| Lanette ® O | Cetearyl alcohol | 3.00 | 3.00 |
| Tegosoft ® MM | Myristyl myristate | 1.00 | 1.00 |
| PCL-Liquid 100 | Cetearyl ethylhexanoate | 1.00 | 1.00 |
| Isodragol ® | Triisononanoin | 3.00 | 3.00 |
| Dragoxat ® 89 | Ethylhexyl isononanoate | 4.00 | 4.00 |
| Avocado oil | Persea gratissima (avocado) oil | 3.00 | 3.00 |
| Abil ® 350 | Dimethicone | 0.50 | 0.50 |
| Covi-ox ® T-70 | Tocopherol | 0.10 | 0.10 |
| Edeta ® BD | Disodium EDTA | 0.10 | 0.10 |
| Carbopol ® Ultrez 21 | Acrylates/C10-30 alkyl acrylate crosspolymer | 0.30 | 0.30 |
| Keltrol ® CG-RD | Xanthan gum | 0.15 | 0.15 |
| Water | Water (aqua) | q.s.p. 100 | q.s.p. 100 |
| Glycerol 99.5 P. | Glycerol | 4.00 | 4.00 |
| Propylene glycol-1,2 99 P GC | Propylene glycol | 3.00 | 3.00 |
| Euxyl ® K712 | Sodium benzoate, potassium sorbate | 0.80 | 0.80 |
| SymMatrix ® | Maltodextrin, Rubus fruticosus (blackberry) leaf extract | 0.50 | 0.50 |
| Sodium hydroxide 10% solution | Sodium hydroxide | 0.50 | 0.50 |
| Perfume oil P2, P4, P6 or P7 | Perfume | 0.30 | — |
| Perfume oil P1, P3 or P5 | Perfume | — | 0.30 |
| Concentrated Herba Santa extract (*E. angustifolium*) as per Example 4 (10% in ethanol) | | 0.10 | — |
| Concentrated Herba Santa extract (E. californicum) as per Example 8 (10% in ethanol) | | — | 0.10 |

Use Example 34

Antiwrinkle Cream

| Ingredients | Weight % | Weight % |
|---|---|---|
| Glyceryl stearate citrate | 1.00 | 1.00 |
| Glyceryl laurate | 1.00 | 1.00 |
| Cetearyl alcohol, | 2.00 | 2.00 |
| Myristyl myristate | 1.00 | 1.00 |
| Cetearyl ethylhexanoate | 4.00 | 4.00 |
| Mineral oil | 4.00 | 4.00 |
| Cyclopentasiloxane, cyclohexasiloxane | 0.50 | 0.50 |
| Acrylate/C10-30 alkylarylate crosspolymer | 0.20 | 0.20 |
| Preservative (phenoxyethanol) | 1.00 | 1.00 |
| Water | q.s.p. 100 | q.s.p. 100 |
| Xanthan gum | 0.10 | 0.10 |
| 1,2-hexanediol | 2.00 | 2.00 |
| Sodium hydroxide 10% soln. | 0.10 | 0.10 |
| *Narcissus Tazetta* extract | 1.00 | 1.00 |
| Perfume oil P2, P4, P6 or P7 | 0.30 | — |
| Perfume oil P1, P3 or P5 | — | 0.30 |
| Concentrated Herba Santa extract (*E. angustifolium*) as per Example 4 (10% in ethanol) | 0.10 | — |
| Concentrated Herba Santa extract (*E. californicum*) as per Example 8 (10% in ethanol) | — | 0.10 |

Use Example 35

Washing and Cleansing Gel

| Ingredient | INCI | Weight % | Weight % |
|---|---|---|---|
| Water | Water (aqua) | q.s.p. 100 | q.s.p. 100 |
| Pionier ® NP 37 G | Sodium carbomer | 1.50 | 1.50 |
| SymSol ® PF-3 | Water (aqua), pentylene glycol, sodium lauryl sulphoacetate, sodium oleoyl sarcosinate, sodium chloride, disodium sulphoacetate, sodium oleate, sodium sulphate | 5.00 | 5.00 |
| Hydroviton ® 24 | Water (aqua), pentylene glycol, glycerol, sodium lactate, lactic acid, serine, urea, sorbitol, sodium chloride, allantoin | 1.00 | 1.00 |
| Extrapone ® Silk GW | Water (aqua), glycerol, hydrolyzed silk | 1.00 | 1.00 |
| Hydrolite ® 5 Preservative | Pentylene glycol Phenoxyethanol | 4.00 | 4.00 |
| Actipearls Red Star # DH10402/6 | Water (aqua), propylene glycol, algin, gellan gum, xanthan gum, calcium chloride, CI 12490 (Pigment Red 5), mica (CI 77019), titanium dioxide (CI 77891) | 1.00 | 1.00 |
| Perfume oil P2, P4, P6 or P7 | Perfume | 0.50 | — |
| Perfume oil P1, P3 or P5 | Perfume | — | 0.50 |
| Herba Santa extract (*E. angustifolium*) as per Example 1 (10% in ethanol) | | 0.2 | — |
| Concentrated Herba Santa extract (*E. californicum*) as per Example 7 (10% in ethanol) | | — | 0.25 |

Use Example 36

Sunscreen Spray

| Ingredient | INCI | Weight % | Weight % |
|---|---|---|---|
| Demineralized water | Water (aqua) | 69.40 | 69.40 |
| Glycerol | Glycerol | 4.00 | 4.00 |
| 1,3 Butylene glycol | Butylene glycol | 5.00 | 5.00 |
| D-Panthenol | Panthenol | 0.50 | 0.50 |
| Lara Care A-200 | Galactoarabinan | 0.25 | 0.25 |
| Baysilon oil M 10 | Dimethicone | 1.00 | 1.00 |
| Edeta BD | Disodium EDTA | 0.10 | 0.10 |
| Copherol 1250 | Tocopheryl acetate | 0.50 | 0.50 |
| Cetiol OE | Dicaprylyl ether | 3.00 | 3.00 |
| Neo Heliopan ® HMS | Homosalate | 5.00 | 5.00 |

-continued

| Ingredient | INCI | Weight % | Weight % |
|---|---|---|---|
| Neo Heliopan ® AV | Ethylhexyl methoxycinnamate | 6.00 | 6.00 |
| Neo Heliopan ® 357 | Butyl methoxydibenzoylmethane | 1.00 | 1.00 |
| Corapan TQ | Diethylhexyl naphthalate | 2.00 | 2.00 |
| Alpha Bisabolol | Bisabolol | 0.10 | 0.10 |
| Pemulen TR-2 | Acrylates/C10-30 alkyl acrylate crosspolymer | 0.25 | 0.25 |
| Phenoxyethanol | Phenoxyethanol | 0.70 | 0.70 |
| Solbrol M | Methylparaben | 0.20 | 0.20 |
| Solbrol P | Propylparaben | 0.10 | 0.10 |
| NaOH, 10% | Sodium hydroxide | 0.60 | 0.60 |
| Perfume oil P2, P4, P6 or P7 | Fragrance | 0.20 | — |
| Perfume oil P1, P3 or P5 | Fragrance | — | 0.20 |
| Concentrated Herba Santa extract (*E. californicum*) as per Example 8 (10% in ethanol) | | 0.10 | — |
| Concentrated Herba Santa extract (*E. angustifolium*) as per Example 4 (10% in ethanol) | | — | 0.10 |

Use Example 37

Sunscreen Milk (W/O)

| Ingredients | INCI | Weight % | Weight % |
|---|---|---|---|
| Dehymuls PGPH | Polyglyceryl-2 dipoly-hydroxystearate | 3.00 | 3.00 |
| Beeswax 8100 | Beeswax | 1.00 | 1.00 |
| Monomuls 90-O-18 | Glyceryl oleate | 1.00 | 1.00 |
| Zinc stearate | Zinc stearate | 1.00 | 1.00 |
| Cetiol SN | Cetearyl isononanoate | 5.00 | 5.00 |
| Cetiol OE | Dicaprylyl ether | 5.00 | 5.00 |
| Tegosoft TN | C12-15 alkyl benzoate | 4.00 | 4.00 |
| Vitamin E | Tocopherol | 0.50 | 0.50 |
| Neo Heliopan ® OS | Ethylhexyl salicylate | 5.00 | 5.00 |
| Neo Heliopan ® AV | Ethylhexyl methoxycinnamate | 7.50 | 7.50 |
| Uvinul ® T150 | Ethylhexyl triazone | 1.50 | 1.50 |
| Demin. water | Water (aqua) | q.s.p. 100 | q.s.p. 100 |
| Trilon BD | Disodium EDTA | 0.10 | 0.10 |
| Glycerol | Glycerol | 5.00 | 5.00 |
| Solbrol M | Methylparaben | 0.20 | 0.20 |
| Phenoxyethanol | Phenoxyethanol | 0.70 | 0.70 |
| Solbrol P | Propylparaben | 0.10 | 0.10 |
| Neo Heliopan ® AP 10% solution, neutralized with NaOH | Disodium phenyl dibenzimidazole tetrasulphonate | 15.00 | 15.00 |
| Perfume oil P2, P4, P6 or P7 | Perfume | 0.25 | — |
| Perfume oil P1, P3 or P5 | Perfume | — | 0.25 |
| Herba Santa extract (*E. angustifolium*) as per Example 1 (10% in ethanol) | | 0.15 | — |
| Concentrated Herba Santa extract (*E. angustifolium*) as per Example 4 (10% in ethanol) | | — | 0.1 |
| Alpha bisabolol | Bisabolol | 0.10 | 0.10 |

Use Example 37

After-Sun Gel

| Ingredients | INCI | Weight % | Weight % |
|---|---|---|---|
| SymSol ® PF-3 | Water (aqua), pentylene glycol, sodium lauryl sulphoacetate, sodium oleoyl sarcosinate, sodium chloride, disodium sulphoacetate, sodium oleate, sodium sulphate | 3.000 | 3.000 |
| Glycerol 99.5 P. | Glycerol | 5.000 | 5.000 |
| SymHelios ® 1031 | Benzylidene dimethoxydimethylindanone | 0.100 | 0.100 |
| Water | Water (aqua) | q.s.p. 100 | q.s.p. 100 |
| Pemulen ® TR-2 | Acrylates/C10-30 alkyl acrylate crosspolymer | 1.000 | 1.000 |
| D-Panthenol 75 W | Panthenol | 0.500 | 0.500 |
| SymFinity ® 1298 | *Echinacea Purpurea* extract | 0.100 | 0.100 |
| Extrapone ® Pearl GW | Water (aqua), glycerol, hydrolyzed pearl, xanthan gum | 1.000 | 1.000 |
| Sodium hydroxide 10% soln. | Sodium hydroxide | 2.500 | 2.500 |
| Preservatives | Methyl, butyl, ethyl, propylparaben, phenoxyethanol | 1.000 | 1.000 |
| Ethanol 96% | Alcohol denat. | 15.000 | 15.000 |
| Perfume oil P2, P4, P6 or P7 | Perfume | 0.20 | — |
| Perfume oil P1, P3 or P5 | Perfume | — | 0.20 |
| Herba Santa extract (*E. angustifolium*) as per Example 1 (10% in ethanol) | | 0.1 | — |
| Concentrated Herba Santa extract (*E. angustifolium*) as per Example 4 (10% in ethanol) | | — | 0.05 |

Use Example 38

After-Sun Lotion

| Ingredients | Weight % | Weight % |
|---|---|---|
| Acrylat/C10-30 alkyl acrylate crosspolymer | 0.4 | 0.4 |
| Cetearyl ethylhexanoate | 15.0 | 15.0 |
| Bisabolol | 0.2 | 0.2 |
| Tocopheryl acetate | 1.0 | 1.0 |
| Panthenol | 1.0 | 1.0 |
| Alcohol | 15.0 | 15.0 |
| Glycerol | 3.0 | 3.0 |
| Perfume oil P2, P4, P6 or P7 | 0.30 | — |
| Perfume oil P1, P3 or P5 | — | 0.30 |
| Herba Santa extract (*E. angustifolium*) as per Example 1 (10% in ethanol) | 0.25 | — |
| Concentrated Herba Santa extract (*E. angustifolium*) as per Example 4 (10% in ethanol) | — | 0.15 |
| Pentylene glycol | 4.0 | 4.0 |
| Preservatives (methyl, butyl, ethyl, propylparaben, phenoxyethanol) | 1.0 | 1.0 |
| Demin. water | q.s.p. 100 | q.s.p. 100 |
| Triethanolamine | 0.2 | 0.2 |

Use Example 39

Solution for Wet Wipes

| Ingredients | INCI | Weight % | Weight % |
|---|---|---|---|
| SymSol ® PF-3 | Water (aqua), pentylene glycol, sodium lauryl sulphoacetate, sodium oleoyl sarcosinate, sodium chloride, disodium sulphoacetate, sodium oleate, sodium sulphate | 2.00 | 2.00 |
| Dragosantol ® 100 | Bisabolol | 0.10 | 0.10 |
| Glycerol 99.5 P. | Glycerol | 5.00 | 5.00 |
| Water | Water (aqua) | q.s.p. 100 | q.s.p. 100 |
| Hydrolite ® 5 | Pentylene glycol | 5.00 | 5.00 |
| Preservative | Phenoxyethanol | | |
| D-Panthenol 75 W | Panthenol | 0.80 | 0.80 |
| DragoCalm ® | Water (aqua), glycerol, Avena sativa (oat) kernel extract | 1.00 | 1.00 |
| Hamamelis Distillate | Hamamelis virginiana (witch hazel) water, water (aqua), alcohol | 1.0 | 1.00 |
| Allplant Essence ® Org. Rose Geranium P | Pelargonium graveolens flower/leaf/stem water | 1.00 | 1.00 |
| Perfume oil P2, P4, P6 or P7 | Perfume | 0.10 | — |
| Perfume oil P1, P3 or P5 | Perfume | — | 0.10 |
| Herba Santa extract as per Example 1 (*E. angustifolium*)(10% in ethanol) | | 0.30 | — |
| Concentrated Herba Santa extract (*E. californicum*) as per Example 8 (10% in ethanol) | | — | 0.20 |

EXAMPLE TS

Test Study

TS1: Antiinflammatory Action in LPS-Induced Human Monocytes

The antiinflammatory test was performed in a cell culture system using human monocytes. Human monocytes are one of the main cell types which are involved in inflammatory processes in tissues; they are the cells which are mainly influenced by the lipopolysaccharides (LPS) produced by gram-negative bacteria. Further, they represent the first step in the cascade of the inflammatory reactions, in that they release various cytokines, e.g. interleukin-1beta, interleukin-6, interleukin-8 and tumour necrosis factor alpha (TNFα), but also other inflammation parameters (e.g. prostaglandin E2). The parameters measured here are recognized inflammation mediators. The use of primary human monocytes enables a realistic portrayal of the pathophysiological situation.

For the experiments, human primary monocytes were sown into 24-well plates (ca. 500,000 cells/ml in 1 ml). The cell viability was determined by means of the AlamarBlue method or by measurement of the intracellular ATP level.

The cells were incubated with the stimulus (LPS) for 24 hrs. Solutions of the *Herba Santa* crude extract, two flavonoid fractions and HED (present as $Na^+$ salt) were added 30 mins before the treatment with LPS. After 24 hrs, the supernatant was removed, centrifuged and investigated according to the operating instructions of the particular manufacturer of the immunoassay used.

The invention claimed is:

1. A mixture consisting of at least two different compounds of the formula (X) or salts thereof:

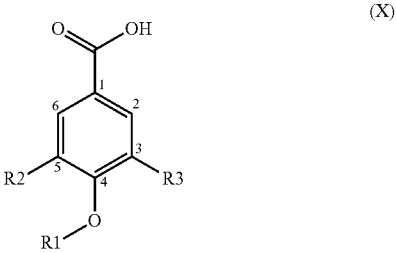

wherein for

R1, R2 and R3 independently of one another in every compound of the formula (X) the following applies:

R1 is hydrogen or methyl,

R2 is an organic residue with 5 carbon atoms and one oxygen atom or none and

R3 is an organic residue with 10 carbon atoms and one or more oxygen atoms, or

R1 and R2 together with the carbon atoms in positions 4 and 5 and the oxygen atom bound to the carbon atom in position 4 form a ring and comprise 5 carbon atoms and one oxygen atom or none, and R3 is an organic residue with 10 carbon atoms and one or more oxygen atoms.

2. The mixture of claim 1, consisting of at least two different compounds of the formula (X) selected from the group consisting of the compounds (1) to (10):

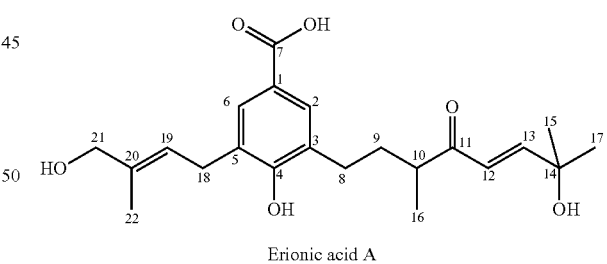

Erionic acid A

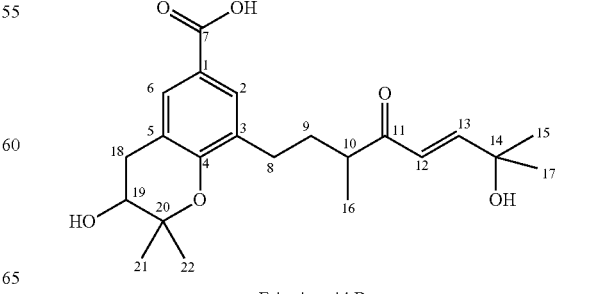

Erionic acid B

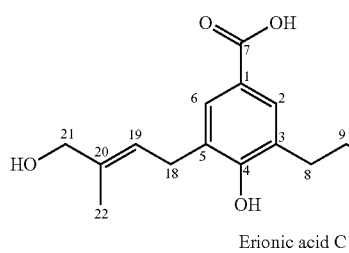

Erionic acid C (3)

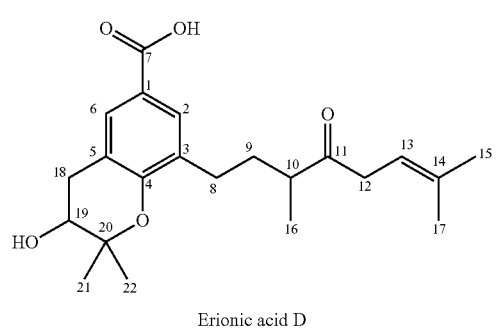

Erionic acid D (4)

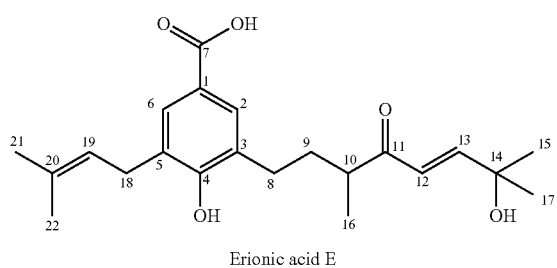

Erionic acid E (5)

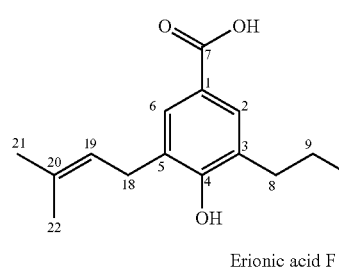

Erionic acid F (6)

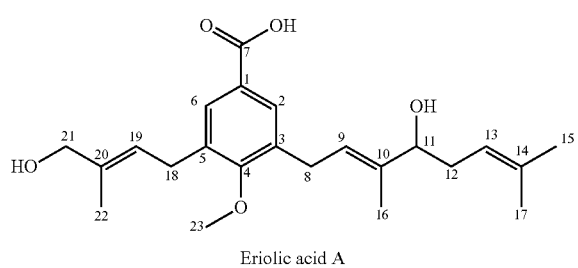

Eriolic acid A (7)

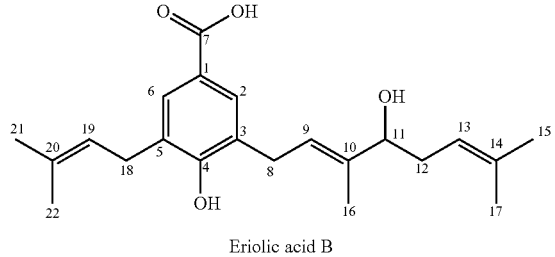

Eriolic acid B (8)

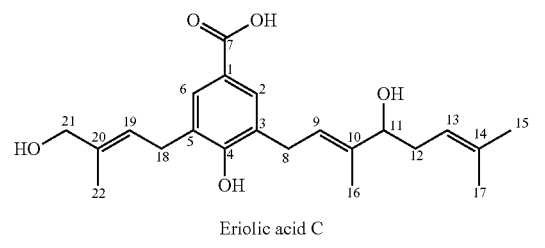

Eriolic acid C (9)

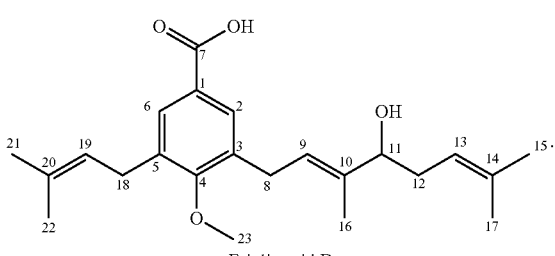

Eriolic acid D (10)

3. A mixture of claim 1, additionally comprising a hydroxyflavone of the formula (Y)

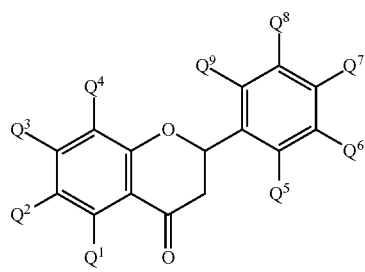

(Y)

or a salt of a hydroxyflavone of the formula (Y) or a mixture containing or consisting of two or more different hydroxyflavones of the formula (Y), two or more different salts of hydroxyflavones of the formula (Y) or one or more different hydroxyflavones of the formula (Y) and one or more different salts of hydroxyflavones of the formula (Y), wherein for Q1, Q2, Q3, Q4, Q5, Q6, Q7, Q8 and Q9 independently of one another in each hydroxyflavone of the formula (Y) the following applies: Q1 to Q9 independently of one another is hydrogen atoms, hydroxy groups, methyl, ethyl, 1-propyl, methoxy, ethoxy, 1-propyloxy or 2-propyloxy groups, with the proviso that at least one of the residues Q1 to Q9 represents a hydroxy group.

4. The mixture of claim 3, wherein the following applies: Q2, Q4, Q5, Q8 and Q9 represent hydrogen atoms, Q1, Q3 and Q6 independently of one another are hydrogen atoms, hydroxy or methoxy groups, with the proviso that at least one of the residues Q1 and Q3 represents a hydroxy group and Q7 represents a hydroxy group.

5. The mixture of claim 3, containing one, several or all compounds of the formula (Y) selected from the group consisting of homoeriodictyol, sterubin, eriodictyol, hesperetin, chrysoeriol and luteolin.

6. The mixture of claim 3, wherein the proportion of the total quantity of compounds of the formula (X) and salts of compounds of the formula (X) in the mixture, based on the total weight of the mixture, is 1 to 99 wt. %, and/or
the proportion of the total quantity of compounds of the formula (Y) and salts of compounds of the formula (Y) in the mixture, based on the total weight of the mixture, is 1 to 99 wt. %.

7. The mixture of claim 3, wherein the proportion of the total quantity of compounds of the formula (X), compounds of the formula (Y), salts of compounds of the formula (X) and salts of compounds of the formula (Y) in the mixture, based on the total weight of the mixture, is 0.0001 to 100 wt. %.

8. The mixture of claim 3, wherein the mixture comprises a plant extract or consists thereof, and the proportion of the total quantity of compounds of the formula (X) and salts of compounds of the formula (X) in the mixture, based on the total weight of the mixture, is 0.1 to 100 wt. %.

9. The mixture of claim 8, wherein the plant extract is an extract from *Eriodictyon* ssp.

10. The mixture of claim 3, wherein the ratio of the total quantity of compounds of the formula (X) and salts of compounds of the formula (X) to the total quantity of compounds of the formula (Y) and salts of compounds of the formula (Y) lies in the range from 0.00001:1 to 1:0.00001 based on the weight.

11. A food, enjoyment, pharmaceutical, medicinal, cosmetic or dermatological preparation comprising an inflammation prophylaxis and/or inflammation treatment effective amount of compound of the formula (x), or a salt or a mixture thereof,

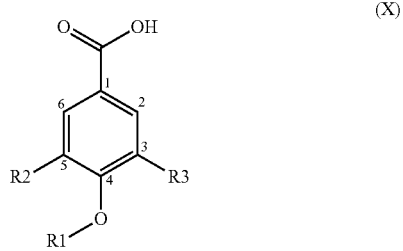

wherein for
R1, R2 and R3 independently of one another in every compound of the formula (X) the following applies:
R1 is hydrogen or 4 methyl
R2 is an organic residue with 5 carbon atoms and one oxygen atom or none and
R3 is an organic residue with 10 carbon atoms and one or more oxygen atoms,
or
R1 and R2 together with the carbon atoms in positions 4 and 5 and the oxygen atom bound to the carbon atom in position 4 form a ring and comprise 5 carbon atoms and one oxygen atom or none,
and
R3 is an organic residue with 10 carbon atoms and one or more oxygen atoms for the prophylaxis and/or treatment of inflammation.

12. The preparation of claim 11, additionally containing one or more further components selected from the group consisting of probiotic bacteria, prebiotics, synbiotics, ballast substances, whey proteins, soya proteins, minerals, tocopherols, vanilla, vanilla extracts, omega-3 fatty acids, citrus, apple, grape seed, green tea, rosemary, tarragon, thyme, horseradish and mace extracts, tannins, tomato, melon and rosehip extracts, beta-carotene; aubergines, rhubarb, red onions, red cabbage, black carrot, superfruits, açai, noni, goji, pomegranate, mangosteen, currants, strawberries, aronia, blueberries and/or elderberries, in the form of dried fruit, extracts or fruit preparations; soya isoflavones, nonsteroidal antiinflammatory drugs, antibiotics, budesonide, systemically active steroids, sulfasalazine, azathioprine/6-mercaptopurine, methotrexate, anti-TNF-alpha antibodies, bisabolol, sodium laurylsulphate, chiorhexidine, metal fluorides, organic and inorganic fluorides, flavourings, essential oils, cooling active substances, menthol, extracts of pure substances from eucalyptus, thyme, wintergreen, spearmint and peppermint.

13. The preparation of claim 11, for the treatment of animal or human skin which requires a treatment with anti-inflammatory active substances.

14. A method for the prophylaxis and/or treatment of inflammation comprising administering a compound of the formula (X), or a salt or a mixture thereof,

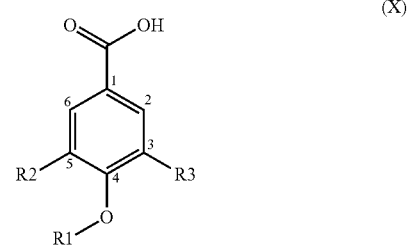

wherein for
R1, R2 and R3 independently of one another in every compound of the formula (X) the following applies:
R1 is hydrogen or methyl
R2 is an organic residue with 5 carbon atoms and one oxygen atom or none and
R3 is an organic residue with 10 carbon atoms and one or more oxygen atoms, or
R1 and R2 together with the carbon atoms in positions 4 and 5 and the oxygen atom bound to the carbon atom in position 4 form a ring and comprise 5 carbon atoms and one oxygen atom or none,
and
R3 is an organic residue with 10 carbon atoms and one or more oxygen atoms.

15. The method of claim 14 for at least one of
a) prophylaxis and/or treatment of inflammation of the skin,
b) reducing the release of TNF-alpha,
c) reducing the release of an interleukin,
d) reducing the release of a prostaglandin, or
e) reducing the release of interferon-gamma and/or NF-κB.

16. The method of claim 14, wherein the method for the prophylaxis and/or treatment of inflammation is or comprises (a) a method for the prophylaxis and/or treatment of chronic inflammatory diseases and/or
(b) a method for strengthening damaged or undamaged skin, and/or
(c) a method for reducing tissue damage, and/or
(d) a method for recreating a normal cellular composition in the intestine, and/or
(e) a method for recreating or stabilizing the function of skin.

17. A process for obtaining the mixture of claim 8 comprising the following steps:
    (a) extraction of plant material from *Eriodictyon* ssp., so that a mixture is formed which contains compounds of the formula (X), optionally compounds of the formula (Y) and other extracted compounds, and
    (b) concentration of extracted compounds of the formula (X) and/or salts of the extracted compounds of the formula (X) and optionally compounds of the formula (Y) and/or salts of the extracted compounds of the formula (Y) in the mixture by partial or complete removal of other extracted compounds and optionally removal of extractants and/or solvents.

18. The process of claim 17, wherein the proportion of the total quantity of compounds of the formula (X) and salts of compounds of the formula (X) in the mixture based on the total weight of the mixture is 0.1 to 100 wt. %.

* * * * *